US006762297B2

(12) United States Patent
Kim et al.

(10) Patent No.: US 6,762,297 B2
(45) Date of Patent: Jul. 13, 2004

(54) EXPRESSION VECTOR CONTAINING LECTIN GENE REGULATION SITE OF MUD LOACH

(75) Inventors: Dong Soo Kim, Pusan Metropolitan (KR); Yoon Kwon Nam, Pusan Metropolitan (KR); Jae Koo Noh, Seoul (KR)

(73) Assignee: Pukyong National University (KR)

( * ) Notice: Subject to any disclaimer, the term of this patent is extended or adjusted under 35 U.S.C. 154(b) by 0 days.

(21) Appl. No.: 10/020,695

(22) Filed: Dec. 12, 2001

(65) Prior Publication Data

US 2003/0140355 A1 Jul. 24, 2003

(30) Foreign Application Priority Data

Dec. 3, 2001 (KR) ........................................ 2001-75877

(51) Int. Cl.[7] .............................................. C07H 21/04
(52) U.S. Cl. ................................... 536/24.1; 536/24.31
(58) Field of Search .............................. 536/23.1, 24.1, 536/24.31; 435/320.1; 800/8

(56) References Cited

PUBLICATIONS

"Regulation and expression of transgenes in fish—a review"; Authors: Arati Iyengar, Ferenc Muller and Norman Maclean; Transgenic Research 5, 1996; pp. 147–166.
"Comparison of Traditional Breeding and Transgenesis in Farmed Fish with Implications for Growth Enhancement and Fitness"; Authors: R.A. Dunham and R.H. Devlin; Transgenic Animals in Agriculture; eds. J.D. Murray, G.B. Anderson, A.M. Oberbauer and M.M. McGloughlin; CAB INTERNATIONAL; 1999; pp. 209–222.
"Extraordinary salmon growth"; Authors: Robert H. Devlin, Timothy Y. Yesaki, Carlo A. Biagi, Edward M. Donaldson, Penny Swanson and Woon–Khiang Chan; Scientific Correspondence; Nature, vol. 371; Sep. 15, 1994; pp. 209–210.
"Production of germline transgenic Pacific salmonids with dramatically increased growth performance"; Authors: Robert H. Devlin, Timothy Y. Yesaki, Edward M. Donaldson, Shao Jun Du, and Choy–Leong Hew; Can J. Fish. Aqust Sci. 52; 1995; pp. 1376–1384.
"Transgenic salmon: tailoring the genome for food production"; Authors: C.L. Hew, G.L. Fletcher, and P.L. Davies; Genetics and Breeding; Journal of Fish Biology 47 (Supplement A); The Fisheries Society of the British Isles; 1995; pp. 1–19.

"Expression of a novel piscine growth hormone gene results in growth enhancement in transgenic tilapia (*Oreochromis niloticus*)"; Authors: M. Asisur Pahman, Rohan Mak, Hala Ayad, Alan Smith and Norman Maclean; Transgenic Research 7; Chapman & Hall; 1998; pp. 357–369.
"Growth enhancement in transgenic tilapia by ectopic expression of tilapia growth hormone"; Authors: Rebeca Martinez, et al.; Molecular Marine Biology and Biotechnology 5(1); Blackwell Science, Inc.; 1996; pp. 62–70.
"Growth performance studies in transgenic Cyprinus carpio"; Authors: Yaniv Hinits and Boaz Moav; Aquaculture 173; Elsevier Science B.V.; 1999; pp. 285–296.
"Dramatically accelerated growth and extrordinary gigantism of transgenic mud loach Misgurnus mizolepis"; Authors: Yoon Kwon Nam, Jae Koo Noh; Young Sun Cho, Hyo Jong Cho, Kyu–Nam Cho, Chul Geun Kim and Dong Soo Kim; Transgenic Research 10; Kluwer Academic Publishers; 2001; pp. 353–362.
"Growth and feed utilization by F4 human growth hormone transgenic carp fed diets with different protein levels"; Authors: C. Fu, Y. Cui, S. S. O. Hung and Z. Zhu; Journal of Fish Biology 53, Article No. jb980686; The Fisheries Society of the British Isles; 1998; pp. 115–129.

*Primary Examiner*—Joseph T. Woitach
(74) *Attorney, Agent, or Firm*—Cantor Colburn LLP

(57) ABSTRACT

Disclosed herein are an isolated polynucleotide comprising a lectin gene regulation site of a mud loach, expressed as SEQ ID NO: 1, an expression vector comprising a lectin gene regulation site of a mud loach, an expression vector comprising a lectin gene regulation site of a mud loach and a growth hormone gene of a mud loach, and an expression vector comprising a lectin gene regulation site of a mud loach and a growth hormone gene of a carp. Also provided a method of making a transgenic mud loach or carp comprising microinjecting the expression vector of a growth hormone gene into fertilized eggs of a mud loach or carp and culturing the eggs such that the eggs hatch and result in a mud loach or carp fish which expresses the growth hormone gene at levels which increase the rate of growth of the fish relative to wild-type mud loach or carp, and a mud loach or carp transformed with the expression vector. The transgenic mud loach or carp shows a stabilized improvement of growth rate without such adverse effect as excessive growth acceleration and has a significantly improved feed conversion efficiency, therefore, improving the culturing productivity.

2 Claims, 17 Drawing Sheets

FIG. 2A

```
-2424                                                           caggtgaggtcgcgcaccaaggct
-2400 aaggccgatcgccaccagtcgaagcctccccgttacgtcgtcggtca████████████agaacattccgat   lecP 1F
-2320 gcgttccgtctcgaataaacttgctcccaaatttattggcccgttttctgttaccaagatcattaatccggtaacagtgc
-2240 gtctgagccttcctccggcgtacaggaaggttcacctgtgttccacgtctccaatattaaaccggtgattttttcccgt
-2160 cttaatccgcctgccccggttccccccccgcctcgtctgttaatggggaaccgacttattcggttaatcgtattctgga
-2080 ctccagacggaggggacgcggatttcagtacttggtggattgggaaggttacggtccggaggagagaaggtgggttcctg
-2000 ctcgggacatactggatcaccgccttatcgatgtttacaatcaacaggtaaagcaggctgggaacgtcaaggggcgttcc
-1920 taggggagggggtactgtcacggtaggaaatcctctgtttcctccgtgtcatgtttgtgtgtgtgtgtttgttactct
-1840 ctgctctgccatgtgctcattaggctgatgtcgctcacctgtgtgttaattgcctcgctccagctgctcatcattacatc
-1760 tcctccataaatactcacatgactctctgttccctgccagatgatcactttctgtttggtcctcgtgttgtgtggttcta
-1680 cgtctcagtcttggattacgaagttgcattgtggattgtttattgtcgtagtcgtcttcgtgtggatgttccgtgtacagt
-1600 ctggattcaccactgctcaccactccaccaacgccgcactcaataaccacctaccaccgtagtcctcgtcaccattgcca
-1520 acaacaccggacatttcctgcttgtgtcatttctctctttgtgtttataaataaacattgtgttttcacctgcaattgct
-1440 tccgctcagttcgtgtcattacaagtacctcaaaatacatattagtatctcaaaggtacatattgctactaaatgtttac
-1360 acatctgtacctaatggtccatacaattaccttttttaaagggtgctgccccagtgacagctagggtacatattttgactt
-1280 ttttctaacaatgtaggtcctaaagggtacggtagactaatctaccaaaattgtattctgttttgtattcctgtaggtac
-1200 caaacagaaacttagggtacagcccagtgacagaaaggtgcagttttgtaccttaatttctgacaatgaacgataaac
-1120 aggaataactaaaacactaccaaatgatactaaaaacgaaagcataaaaagatgaaaactaaaatgcaaagaaaagaaa
-1040 actgaagtgactgagttaaatttatggcagaatgtttcctgtttctgataagatgaaaacctacttctaataacccaaa
- 960 taaccaaataattatctgcaaacattaaagaaactcagttatgcaatctatggtaaatagttactgaaaggaatacaccaa
- 880 tgccaaggttttttgggcaaggagctttgtttacatgatatttacttttttgtgtggtcagatgagctgtccggtggtgggcc
- 800 cgtcggccatggttcaggcttttacgtgctgcaaatgggaatgagtcaggttcagttcaacagcctgaacacgaagtga
- 720 tgtgaaatgctgatcagctgttcagcttaaaaaaagttcatttgctgccttaaaatccaactttaaaatattagttgaca
- 640 caaacagttttaaacagtttctcgttttgagtcaactaatattttaagttgaatgaactcaaaattttaagtcgctttt
- 560 taagttgaaacatttctttaccgtttatatcaagcagactgcaataaaagctcttacaaaaatacttctttgcatgatcac
- 480 acacattaaagaaacacactaaaaatacaaaaataaacaaatctatatatgcaatatatttatataaaatacttgcaata
- 400 aacagtaaaataacaaaatctaatgtaaagacatgagtcaataaaaatatgtaaaacatccataaatgtaaaatatactg
- 320 aaagaaatgtgaacacagaaaagtgttcatgtgtcagatcaggatgtttatttgataaccatcacatttcatcatatat
- 240 tgtatacatatatacaagttcatgatatccagatttactttttcttgtttat██████████████tgaacaaaag   lecP 2FW
- 160 tataaaagatagggactcctcattgaccatcacacaatctacactgaagttctgaaagtgaagatttgacaaaaaggtgag
-  80 ttttataacattaacttcagcagtgtgtacatatgagt████████████████tgttcattcatttcagattcatc   lecP 1R
    1 ATGGCAGTCATGAGAGCTCTTGTGCTTCTTTTCTTGGTCTTTTCTGTTGAGAGTGCACCAGgtaaccaagacgtttacaa
  I   M  A  V  M  R  A  L  V  L  L  F  L  V  F  S  V  E  S  A  P                                    21
   81 gattgaccaaaccctgttaccaatattccagattaaattcccataaaattgtgttttccataaaacttgttaaacattat
  161 aaacatcatgaaaggatgtcaacagaagcaacatttaaagcacttatagacagaaacataaaactaataatgtgactttta
  241 tattactaatattttaatcactgtatagCTCATCGCTGCCCACATGGATGGACACCCTTTGGTGTGCAATGCTACAAATT
  II                             H  R  C  P  H  G  W  T  P  F  G  V  Q  C  Y  K  F   38
  321 CTTCTCTCAGTCAGTTGACTGGATCACAGCTGAGgtactgttattcagttattcaaattgttgaataagaatactcaatg
       F  S  Q  S  V  D  W  I  T  A  E                                               49
```

FIG. 2B

```
 401 tcatgatccaagctgaaacagattagattttatatttgcaataaaataatctctctctctttagAAAAACTGTCAATCTA
III                                                                  K  N  Q  S  I    55
 481 TTGATGCTAATCTTGCATCTGTGCGCAGTACAATGGAACACAACTTTCTCCTGAGTCTGATTGTGTCTGCTAACACACGT
      D  A  N  L  A  S  V  R  S  T  M  E  H  N  F  L  L  S  L  I  V  S  A  N  T  R    81
 561 GTTTGGATTGGTGGCCATGATGGTGAAACTgtaagtcatttttgctctgaaatgctgatattgtcatggctagtctgaaat
      V  W  I  G  G  H  D  G  E  T                                                    91
 641 taatgctttaattataaaactgattttttctatagatacaataactaaatgcttttttgttacaatataaatgattgaatta
 721 tatcataaatgaaaagattattagtaaactctttgactctcctcactcattagGAAGGACAATGGCTGTGGTCTGATGGA
IV                                                        E  G  Q  W  L  W  S  D  G  100
 801 TCTCAATTTCACTTTACCAACTGGTGCCCTGGAGAACCTAGCAATAATTTTGGTAAAGAGAACTGCCTGGAGATAAACTT
      S  Q  F  H  F  T  N  W  C  P  G  E  P  S  N  N  F  G  K  E  N  C  L  E  I  N  F 127
 881 TACACgtaagaaagtctcatatcattattgttttatttacaatcttaaaattctatagcattttgtattaaatttactt
      T  Q                                                                            129
 961 gtttaatgtcagaaaatgctacgtgcagtgtattcactacattcagatccctttaaccttttcagtgttgttatttttgcag
1041 cctgatggtacaattgtttgaattcatacttggttccccataatgaaaaagtgaaaacagaattttataaatgtctgtaa
1121 aaaattttaaaagaaaaaatgtcacatttactgtatttaaaccaagggtgccaaactctgtcttggagggccggtggtga
1201 cctgtgtagtttagctctaacactaatcaaacacacctaaagcagttttattaaagtctaactaagcatactagaaacttc
1281 tagacaggtgagctgagacaagttgaaactaaactctgcaggacaccgggcctctaggaacgagtttgggcacccctgat
1361 ttagacccttttgcaacaacacttgaaattttgctcagatgcctcttgatcgttgctgatttatacatttattttattca
1441 aactacaccggtaatgatcagtactgatttttattttcatcttatcccacagAGAACCGTTGCTGGAATGATGCGGATTGT
V                                                         N  R  C  W  N  D  A  D  C  138
1521 TCAACCACAATCAGCTACATTTGTGCCCAACCTATTAGATCAtgaaaaatcaatctgtttcaaagtactatgattttact
      S  T  T  I  S  Y  I  C  A  Q  P  I  R  S  *                                    152
1601 acatgcctatacatttttttctgatcttattcttaaaactcagtatcttactgaagctttctgaaaacttctccaatcaa
1681 taaaagcatttataaagcaaattgtttgcattgttgagtcaaaaaaattaatcatcaaattaaatacaatataaaaacaaa
1761 acaacaatacatctaaaataacaaaaagggctttcacaattgaaatagttaacctcaggttattctaaaccccaggttta
1841 aagaatcctgggttatctgtttcacgtttcacactgttcatacttaaccaggagggtaaagaaataacccctgggtattcat
1921 aatctgatgtttcacactgtgcatttctaaaccttaagttaatgtttttcatttgcatatttggggtgtcagcaatttaag
2001 gaagtttcttcacctcctcattagcatccagacagcagaagtagggaactgagcagcgttcatgactgaggttctcttca
2081 gaacaactgaagtacattgagactaatccatgtaagagattcctccacagccagtggcatgtttaccatttttggggggtcc
2161 taagcaaagttcaagaaccggggccccccatgccccagcattgcccaaggttttcatttgaattgcacaacaataacat
2241 tcagtatacagaattaagttagatatatataaaccgggtttatttagttgtacctgcttaaagtaacactaaattgtta
2321 cagtatgacaaagattcttatagattcatatatagatgtcttaggatgtatttaaaacaatgtaattaatactgcaactt
2401 cagtgtctgacatcttactaaaaaaactaaatgaggaaaaagaggaagcattagattatgattcagactggtctaacaaa
2481 caccagcaaacaatattgtaagttggttaatgcttgacttaatggatgggaatcacataactctcatgttcatattgcaa
2561 aaacaaacttactgtgagatacaacaagcatatagactagacatacactaaagatgagattttaatgacaatgatgagat
2641 acagaatatgatttatgtattttcgacatgtgtggtgtctttatcatgttaatacctgtacgagcatggaacaaaagatg
2721 cgtgaatgttgtgcagttatgagagcaaagatagagtcgtgtgagcgctcattccagcacttgtgtggctgcatttgtgc
```

FIG. 2C

```
2801 gcgctgagcagaggtccgctttcccgtagagcttcgttcatgaagtagcctttatgtgcccttgcaaggatgtgggcaaa
2881 tattattctgcgtgcatactcacacatctctccctcgcacgtgctttatccgtaccttagatttggttctgaataaacct
2961 aacatactttcgcacaccttgtggccagtagggggcccccaagcctgcgggccctacgcaattgcatggtttgcgtggtg
3041 ggtaaacacgccactggttacattgcaagatactttgtaaaaaaatgttaatctgttaatagtgccctattttaacaatc
3121 taagtgcatggtctaaagtgcaaaagggtttgtcctaatccacttctgctaatttaacgacgggacaaattttggggcgt
3201 ctagcgcactgtcttaaagggttgttcctattctagtaatgagtaatgggtgtgttttgggcatgagttcgattcaatgt
3281 tatttatataaagctttcacaattgtttaattgtttcaaagcagctttacattaaaatatatattactgttttttttaaa
3361 ctgatgtaagattgacacgaacagtgattgttgatttgtatgtgcatcaaggcaaggcaagtttatttgtatagcacatt
3441 tcatacacagaggtcattcaaggtgctttacatagaaatgagaaaacaatatatgagaaaaaaagtatgtagaaaaaaat
3521 caaagatacatttgaatttaaaatatcaattaaaagaaaataaatgtgattttaatagaaactgtttaaatgtgtgaaaa
3601 aaataaagtataaaacagtaaaaaaaaattattattatttagctcagtgggaccatatacaggttgaacaggagtgcttc
3681 ggacaacctgacaattgtcagaatagatcagagaattgcctggaaataaacttttgaagtaagaatgtctattattattg
3761 ttttattataatcttaacattttataggatttagtacacaataagccagtttagctgtcagaaaatgttacgtgcagtg
3841 cattcactacattcagatccctttcatttttattttgttcaatgttgtgtagtgattttgacacgagcaccaattaattta
3921 gtgattttcacatgggcaaccattggttagtagtatgccatacacaggacactagaggtttcagaagtacatgctgggac
4001 caaagagaccttattagtactgtcacggtaggaaatcctctgtttcctccgtgtcatgtttgtgtgtgtgtgtttgtt
4081 actctctgctctgccatgtgctcgttaggctgatgtcgctcacctgtgtgttgattgcctcgctccagctgctcatcatt
4161 acatctcctccataaatactcacatgactctctgttccctgccagatgatcactttctgtttggtcctcgtgttgtgtgg
4241 ttctacgtctcagtcttggattacgagttgcattgtggattgtttattgtcgtcgtcgtcttcgtgtggatgttccgtgt
4321 acagtctggattcaccactgctcaccactccaccaacgccgcactcaataaccacctaccaccgtagtcctcgtcaccat
4401 tgccaacaacaccggacatttcctgcttgtgtcatttctctctctgtgtttataaataaacattgtgttttcacctgcaa
4481 ttgcttccgctcagttcgtgtcattacagaatcatctggccatacatggaagcagcaggagaccaacccacggccacgct
4561 ggaggaatttctccagcgaactctggctcgtatggatcttcaggaccagtcgatcaacgaaatgcgataggccgtccatg
4641 caatgatgacgaaggtgtccgagctctctcagcgttcctctcatccttcgcctcccactgcgccacccacaccgcccgca
4721 ccatcttctcctccaaggggtggttttcctccggagccccgattaccgatccctgagaaatactccggtgagccaaatta
```

FIG. 7
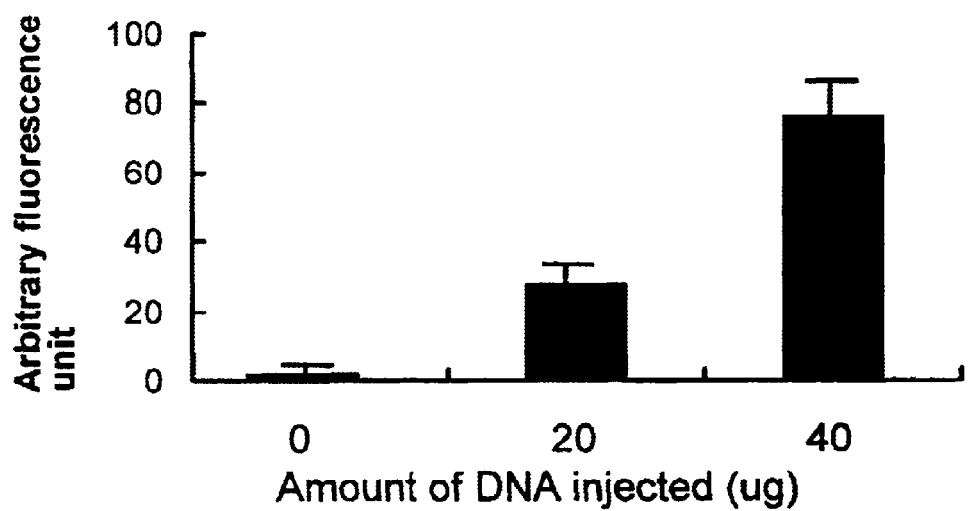
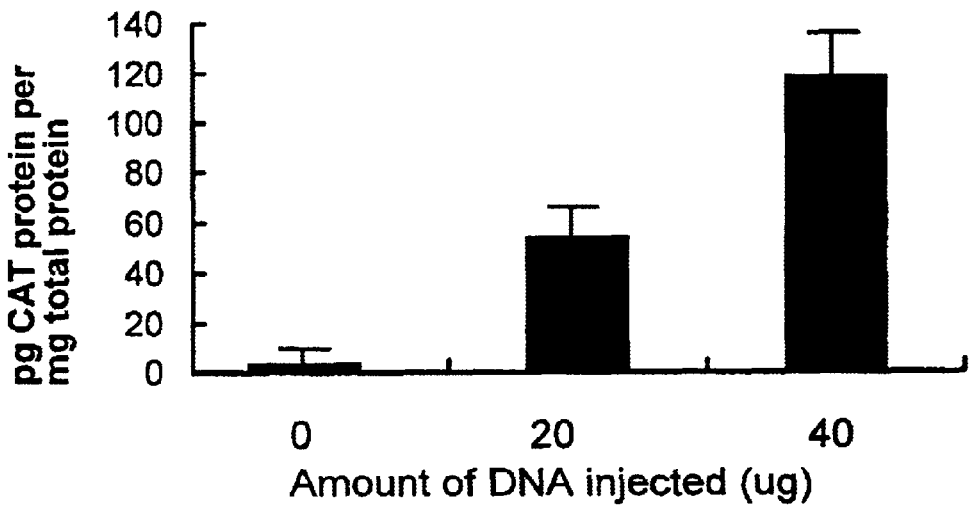

EXPRESSION VECTOR CONTAINING LECTIN GENE REGULATION SITE OF MUD LOACH

BACKGROUND OF THE INVENTION

1. Field of the Invention

The present invention relates to an expression vector containing lectin gene regulation site of mud loach for producing tralsgenic fishes. More particularly, it relates to an expression vector of mud loach or carp growth hormone gene fused to lectin gene regulation site of mud loach, and a method of producing a fast-growing transgenic mud loach or carp by transforming it with the expression vector, and a transgenic mud loach or carp produced thereby.

2. Description of the Related Art

Transgenesis of fish is considered to provide a useful model for the research in expression and regulation of vertebrate genes and to produce a novel fish strain having a useful function; thereby to overcome the limit of productivity increase which remains unsolved in the conventional fish breeding (Iyengar, A., Muller, F. and Maclean, N., 1996. Regulation and expression of transgenes in fish a review. Transgenic Research 5, 147–166; Dunham, R. A., Devlin, R. H., 1999. Comparison of traditional breeding and transgenesis in farmed fish with implications for growth enhancement and fitness. In: Murray, J. D., Anderson, G. B., Oberbauer, A. M., McGloughlin, M. N. (Eds), Transgenic animals in agriculture. CAB International, Wallingford, UK, pp. 209–229). In an early stage of fish transgenesis, mammal or microorganism gene regulation sites are used to produce transgenic fishes. However, since the mammal or microorganism gene regulation sites were known to have little effect on fish cells, many efforts have been made to acquire new fish-originated promoters for developing transgenic fish.

Most of efforts to produce transgenic fishes for increasing productivity have been concentrated on the improvement of growth rate due to the recombination of growth hormone gene. However, for all the attempts at various fishes, successful improvements of growth rate have been limited to several fishes. Further, those fish-originated promoters to be used in fish transgenesis have been also limited to several species and applications. Up to this time, successful examples of improvement of growth rate and transformation have been transfer of the MT promoter of sockeye salmon and AFP promoter of ocean pout fused with salmon growth hormone gene into salmon species (Devlin, R. H., Yesaki, T. Y., Biagi, C. A., Donaldson, E. M., Shan, R. M., 1994. Extraordinary salmon growth. Nature 371, 209–210; Devlin, R. H., Yesaki, T. Y., Donaldson, E. M., Du, S. J., Hew, C. L., 1995. Production of germline transgenic Pacific salmonids with dramatically increased growth performance. Canadian Journal of Fisheries and Aquatic Science 52, 1376–1384; Hew, C. L., Fletcher, G. L. and Davies, P. L., 1995. Transgenic salmon: tailoring the genome for food production. Journal of Fish Biology 47, 1–19) or into tilapia (Rahman, M. A., Mak, R., Ayad, H., Smith, A., and Maclean, N., 1998. Expression of a novel piscine growth hormone gene results in growth enhancement in transgenic tilapia (Orechromis niloticus). Transgenic Research 7, 357–369), transfer of CMV promoter fused with growth hormone gene cDNA of tilapia into tilapia (Martinez, R., Estrada, M. P., Berlanga, J., Guillen, I., Hernandez, O., Cabrera, E., Pimentel, R., Morales, R., Herrera, F., Morales, A., Pina, J. C., Abad, Z., Sanchez, V., Phillippa, M., Lleonar, R. and Fuente, J., 1996. Growth enhancement in transgenic tilapia by ectopic expression of tilapia growth hormone. Molecular Marine Biology and Biotechnology 5, 62–70), transfer of β-actin promoter of carp fused with growth hormone gene cDNA of carp into carp (Hinits, Y. and Moav, B., 1999. Growth performance studies in transgenic Cyprinus carpio. Aquacutlure 173, 285–296), and transfer of expression vector of mud loach growth hormone containing β-actin promoter of mud loach into mud loach (Nam, Y. K., Noh, J. K., Cho, Y. S., Cho, H. J., Cho, K. N., Kim, C. G. and Kim, D. S., 2001. Dramatically accelerated growth and extraordinary gigantism of transgenic mud loach (Misgurnus mizolepis). Transgenic Research 10, 353–362). Except the success of virus-originated CMV promoter transferred into tilapia, promoters and regulation sites of the same or related fish species have been used as expression vectors of growth hormone.

In these successful examples, however, the effects cover a wide range from a limited improvement of growth rate to a greatly accelerated growth rate by dozens of times according to the expression vector and fish species to be used. Further, some promoters have been too effective to result in physiological deformation and adverse effect caused by an excessive expression of growth hormone (Dunham, R.A., Devlin, R.H., 1999).

A mud loach (Misgurnus mizolepis), a representative fresh-water fish species in Korea, has been widely used as an excellent food in Korea and Japan and the scale of its market and consumption is extending. However, due to a contamination of natural basin system and reclamation of rivers, the amount of natural catch decreases every year. Accordingly, culturing of mud loaches becomes inevitable and improvement of its breed through transgenesis is required to increase the productivity in a short time.

A possibility of transforming mud loach has been recognized when an expression vector of mud loach growth hormone gene containing β-actin gene regulation site of mud loach was transferred into a fertilized egg to show a great growth acceleration effect However, since the β-actin promoter to be used for the transgenesis has an excessive activity to various tissues, some of transgenic mud loaches show an excessive growth acceleration and grow to an unnecessary large size; therefore, more stable expression vector is required to be developed (Nam et al., 2001).

A carp (Cyprinus carpio) is one of fishes to be cultured widely in the world containing Korea. For all the attempts to improve carp breeds all over the world, a great increase of productivity is considered to be difficult for some time. Accordingly, transgenic carp of high growth rate are inevitable to increase productivity.

Research in transgenesis targeted on a carp has been made by some of groups. For example, Fu et al. led to a fast-growing carp by using an expression vector containing human growth hormone gene fused with mouse MT promoter (Fu, C., Cui, Y, Hung, S. S. O. and Zhu, Z., 1998. Growth and feed utilization by F4 human growth hormone transgenic carp fed diets with different protein levels. Journal of Fish Biology 53, 115–129), which had only slight improvement of growth rate and gave unwillingness about the genes and regulation sites originated from human. Further, Hinits and Moav (Hinits, Y. and Moav, B., 1999) tried to transform a carp by using carp β-actin promoter and carp growth hormone cDNA, which showed also lower improvement of growth rate than two times except the result of winter period experiment. Therefore, a transgenic carp expected to improve the productivity greatly has not yet been developed.

Considering the above, a transgenesis of mud loach or carp is required to improve their culturing productivity, and therefore, a demand for developing an expression vector which expresses the transferred genes in an effective and stabilized marmer in mud loach or carp and gene regulation site therefor is increasing.

SUMMARY OF THE INVENTION

To improve the culturing productivity by producing a fast-growing transgenic mud loach or carp, it is an object of the present invention to provide a gene regulation site which can express the genes transferred into a mud loach or carp in an effective and stabilized manner, and an expression vector containing the gene regulation site.

It is another object of the present invention to provide a fast-growing mud loach and carp transformed with the expression vector, and a method of producing a fast-growing transgenic mud loach and carp using the expression vector.

To achieve the object of the present invention, there is provided an isolated polynucleotide comprising a lectin gene regulation site of a mud loach, expressed as SEQ ID NO: 1.

In accordance with a further aspect of the present invention, there are provided an expression vector comprising a lectin gene regulation site of a mud loach, an expression vector comprising a lectin gene regulation site of a mud loach and a growth hormone gene of a mud loach, and an expression vector comprising a lectin gene regulation site of a mud loach and a growth hormone gene of a carp.

In accordance with still another aspect of the present invention, there are provided a method of making a transgenic mud loach or carp comprising microinjecting the expression vector into fertilized eggs of a mud loach or carp and culturing the eggs such that the eggs hatch and result in a mud loach or carp fish which expresses the growth hormone gene at levels which increase the rate of growth of the fish relative to wild-type mud loach or carp, and a mud loach or carp transformed with the expression vector.

In the present invention, a lectin gene and regulation site containing its promoter is isolated from a mud loach, and then the lectin promoter is fised with various structural genes (e.g., genes for coding such reporter proteins as CAT or BFP) to construct reporter expression vectors, which confirm the ability of the lectin promoter to induce expressions in vivo. Especially, an expression vector of growth hormone gene containing the lectin gene regulation site of a mud loach is transferred into a mud loach or carp to produce a fast-growing transgenic fish breed, thereby increasing culturing productivity.

BRIEF DESCRIPTION OF THE DRAWINGS

The above object and advantages of the present invention will become more apparent by describing in detail a preferred embodiment thereof with reference to the attached drawings in which:

FIGS. 2a to 2c show the entire DNA sequence of the lectin gene and its regulation site of a mud loach (SEQ. ID. No. 2);

FIG. 7 is a graph showing the expressions of pmlectBFP and pmlectCAT that are transferred into a mud loach liver;

DESCRIPTION OF THE PREFERRED EMBODIMENTS

Figure 1:
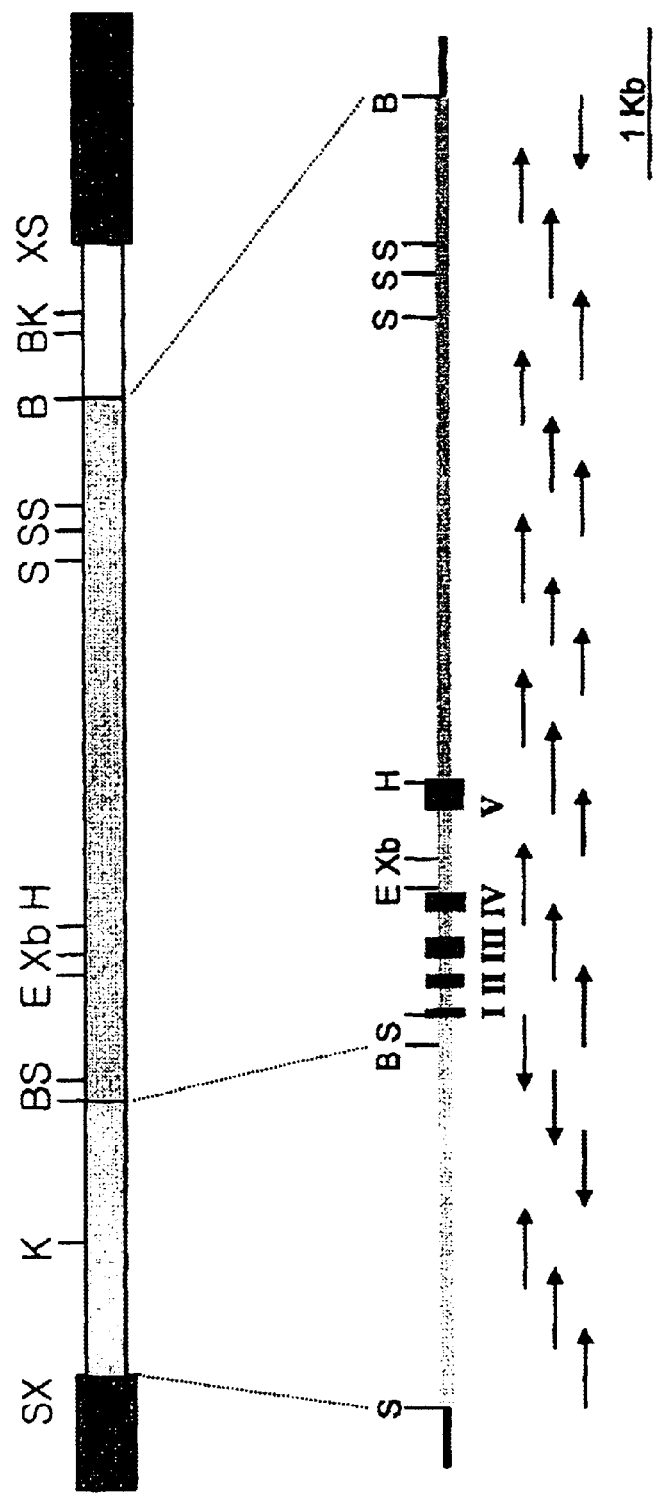
FIG. 1 shows a restriction enyyme map of a phage DNA containing the lectin gene of a mud loach and sequencing strategy.

The present invention will now be described by the following embodiments in more detail with reference to the accompanying drawings. However, these embodiments are illustrations only provided for a better understanding of the invention, not for the purpose of limiting.

The followings are the process of manufacturing a regulation site containing a lectin gene promoter of mud loach, an expression vector of growth hormone containing the regulation site, and a fast-growing mud loach and carp tansformed with the vector.

1. Cloning of the Lectin Gene Reglation Site of a Mud Loach and Examination of its Ability to Induce Gene Expression Using a lectin cDNA expressed in a mud loach liver as a probe, a lectin gene and its regulation site are isolated from a mud loach GDNA library and their sequences are analyzed. With the analysis of DNA sequence, PCR is carried outto obtain the lectin gene regulation site, which is then incorporated into pGEM-T easy vector. A competent bacteria, XL1-Blue MRF' is transformed with the vector and a recombinant plasmid (pmlectP) containing the lectin gene regulation site (2.3 kb) is identified.

Then, an expression vector of BFP (pmlectBFP) and one of CAT (pmlectCAT), both of which contain the lectin gene regulation site of a mud loach, are manufactured After the reporter expression vectors (pmlectBFP and pmlectCAT) are injected into a mud loach liver, PCR analysis of the pmlectBFP and pmlectCAT is carried out to confirm the successful transfer of the BFP and CAT genes. Further, RT-PCR analysis of mRNAs expressed from the pmlectBFP and pmnlectCAT is carried out to confirm their successful expressions in the liver. The expression of BFP protein is identified by fluorometric analysis on the liver tissue transferred with the pmlectBFP. The expression of CAT protein is identified by performing CAT-ELISA on the liver tissue transferred with the pmlectCAT. Accordingly, it is confirmed that the lectin gene regulation site of a mud loach can induce expressions of foreign genes in a mud loach liver.

2. Manufacture of an Expression Vector of a Gowth Hormone Hene Contaning the Lectin Gene Regulation Site of a Mud Loach.

A segment containing lectin gene regulation site (2.3 kb) separated from the pmlectP is ligated with pmlGH, the plasmid containing the growth hormone gene of a mud loach, to obtain an expression vector of a mud loach growth hormone gene containing the lectin gene regulation site of a mud loach (pmlectmGH).

In order to manufacture an expression vector of a carp growth hormone gene containing the lectin gene regulation site of a mud loach (pmlectcGH), the carp growth hormone gene (2.4 kb) separated from a carp gDNA is cloned into pGEM-T-easy vector by TA cloning (pGEMTcGH), from which the carp growth hormone gene (2.4 kb) is recovered by Sac II and then ligated with pmlectP that is digested with the same restriction enzyme.

3. Production of a Fast-gowing Mud Loach and Carp (1) A fast-growing mud loach

The expression vector of a mnud loach growth hormone (pmlectmGH) containing the lectin gene promoter of a mud loach is microinjected into fertilized eggs of a mud loach and hatched to produce a fast-growing tmnsgenic mud loach.

The transgenic groups have shown heavy body weights deviated from a normal distribution and have the growth ratio of seven times higher compared with its normal mud loach sibling. Further, the transgenic male groups randomly selected from the first generation mud loaches have shown incidence of transgenic progeny of 26~42% to make mosaic form of the first generation (F0) transgenic mud loaches. The second generation (F1) tnansgenic groups have shown an acceleration of 6~10 times for the time required to be a commercially available size compared with non-transgenic sibling groups. The feed conversion efficiency of the transgenic mud loach (F1) has been about 1.5 times higher than that of non-transgenic sibling groups.

(2) A fast-growing carp

In order to confirm that the lectin gene promoter according to the present invention can induce the expression of other fishes such as a carp, the expression vector (pmlectcGH) containing a carp growth hormone gene and a lectin gene promoter of a mud loach is microinjected into fertilized eggs of a carp and hatched to produce a transgenic carp.

The body weight distribution of the transgenic groups and non-transgenic groups has shown that the incidence of the fast-growing individuals which laid outside a normal distribution was 23% of the whole microinjected group. In four months after hatched, the cumulative survival ratio of the F0 population of the tnansgenic groups to non-transgenic siblings has shown no significant difference and both groups have survival rates not less than 95%. Further, the transgenic carp groups have significant increase of body weight after 30 days from the beginning of the experiment, and the mean body weight of the transgenic groups has been more than 3 times the weight of non-transgenic siblings on the last seventh month.

The following examples are intended to further illustrate the present invention without limiting its scope.

EXAMPLE 1

Cloning of a Lectin Gene Regulation Site of a Mud Loach and Examination of its Ability to Induce Gene Expression 1. Separation of lectin gene and its regulation site from a gDNA library of a mud loach.

(1) As a probe for identifing a lectin gene from a gDNA library, an EST clone having high affinity with a lectin gene cDNA to be reported was selected among the EST clones expressed in mud loach liver. The probe was probe was labeled with digoxygenin 11-dUTP (Roche Molecular Biochemicals, Germany) by using PCR and used for library search.

(2) The titer of a phage containing a mud loach genornic DNA library was adjusted to make 500,000 plaques through the infection into host cell KW251, on which filter hybridization was carried out using the above probe. For the selection from the genomnic DNA library, ten clones of 50,000 lambda phage plaque were prepared on the culture medium in 150 mm petridish, and the prepared genomic clones were moved into nylon membranes to carry out screening through filter hybridization. The filter hybridization was carried out using Non-radioactive digoxygenin labeling and detection kit (Roche). Screening was carried out three times to each clone selected in the first screening and then the clones indicating 100% positive signal in the last hybridization were selected.

(3) Six positive clones were selected through the above process, from which one positive phage DNA was separated. The separated DNA was digested with one or various combinations of the restriction enzymes including BamHI, EcoRI, HindIII, SacI, KpnI, XbaI, XhoI, and PstI, and then restriction enzyme map was made by comparing the size of the segments on electrophoresis. To identify a segment containing the lectin gene, Southern blot was carried out using the probe prepared in the process of (1). The lectin gene segment was recovered through the treatment with restriction enzymes and subcloned into the plasmid vector, pBlueScript II KS (−)(Stratagene, USA).

(4) The restriction enzyme map of the subcloned lectin gene was made according to the process of (3). Based on the map, the segments of which one ends were deleted successively were subcloned again and the DNA sequence was analyzed by means of the erase-a-base method using exonuclease III. FIG. 1 shows a restriction enzyme map of a phage DNA containing the lectin gene of a mud loach and sequencing strategy.

DNA sequence of each subcloned segment was analyzed using ABI 377 automatic sequence analyzer (PE Biosystem, USA) and Bigdye Terminator Sequencing kit (PE Biosystem, USA) and the sequence of each segment was combined into the entire DNA sequence using sequencing software Sequencher (GeneCodes, USA).

Analysis of the amino acid sequence and gene information by means of searching GenBank for the entire DNA sequence indicates that the separated gene is C-type lectin. FIG. 2 shows the entire DNA sequence of the lectin gene and its regulation site of a mud loach. In FIG. 2, the underlined part is the lectin gene regulation site of a mud loach that is used in the expression vector of the present invention.

SEQ. ID. No: 1 shows the DNA sequence of the lectin gene regulation site of a mud loach and SEQ. ID. No: 2 shows the entire DNA sequence of the lectin gene and its regulation site of a mud loach.

(5) With reference to the above DNA sequence, a translation start codon ATG was identified. Based on the restriction enzyme map information of the phage DNA, the 5' upper part containing the translation start codon was subcloned into the plasmid pBS II KS and the DNA sequence was analyzed (FIG. 2). To separate the 5'-upstream regulation site of 2.32 kb to be required, a forward primer lecP 1F and reverse primer lecP 1R were determined as follows:

lecP 1F: 5'-AAG AGT GTG GCT TTG ACC C-3' (SEQ. ID. No: 8)

lecP 1R: 5'-GGA AAA GTG ACA CAT CTG C-3' (SEQ. ID. No: 9)

Using these primers, PCR was carried out on the templates of the phage DNA containing the lectin gene regulation site under the following condition.

(Composition of solution for PCR)

| | |
|---|---|
| Distilled water | 28 µl |
| 10X PCR buffer with 15 mM MgCl$_2$ (Roche) | 5 µl |
| 10X dNTPs (each 2.5 mM) | 5 µl |
| 5 uM of forward primer lecP 1F | 5 µl |
| 5 uM of reverse primer lecP 1R | 5 µl |
| Taq DNA polymerase (Roche, 5 unit/µl) | 1 µl |
| Template DNA (50 ng/µl) | 1 µl |

(Condition for PCR)

1 cycle: Initial denaturation at 94° C. for 2 minutes 30 cycles: Denaturation at 94° C. for 1 minute, annealing at 60° C. for 30 seconds, and extension at 72° C. for 1 minute and 30 seconds.

1 cycle: Final extension at 72° C. for 5 minutes (6) For only the regulation site to be cloned into the plasmid vector, residual primers and dNTPs were removed from the PCR products by PCR purification system (Promega). After the purification, the regulation site, was ligated with pGEM-T easy vector (Promega). The ligation was carried out in the following solution at 4° C. for 12 hours.

(Composition of ligation mixture solution)

| | |
|---|---|
| 2X T4 ligase buffer | 5 µl |
| pGEM-T easy vector | 1 µl (50 ng) |
| PCR product | 1 µl (100 ng) |
| Distilled water | 2 µl |
| T4 DNA ligase | 1 µl |

After the completion of ligation, 5 µl of the ligation mixture was used to transform competent bacteria (XL1-Blue MRF') by CaCl$_2$ method. The recombinant plasmid containing the correct PCR product (2.3 kb of lectin regulation site) was identified and named pmlectP. The plasmid pmlectP was introduced into *E. coli* XL1-Blue MRF' and deposited with the KCTC as accession number KCTC 10124BP on Nov. 22, 2001.

2. Manufacture of an Expression Vector of a Reporter Gene Containing the Lectin Gene of a Mud Loach.

Figure 3:
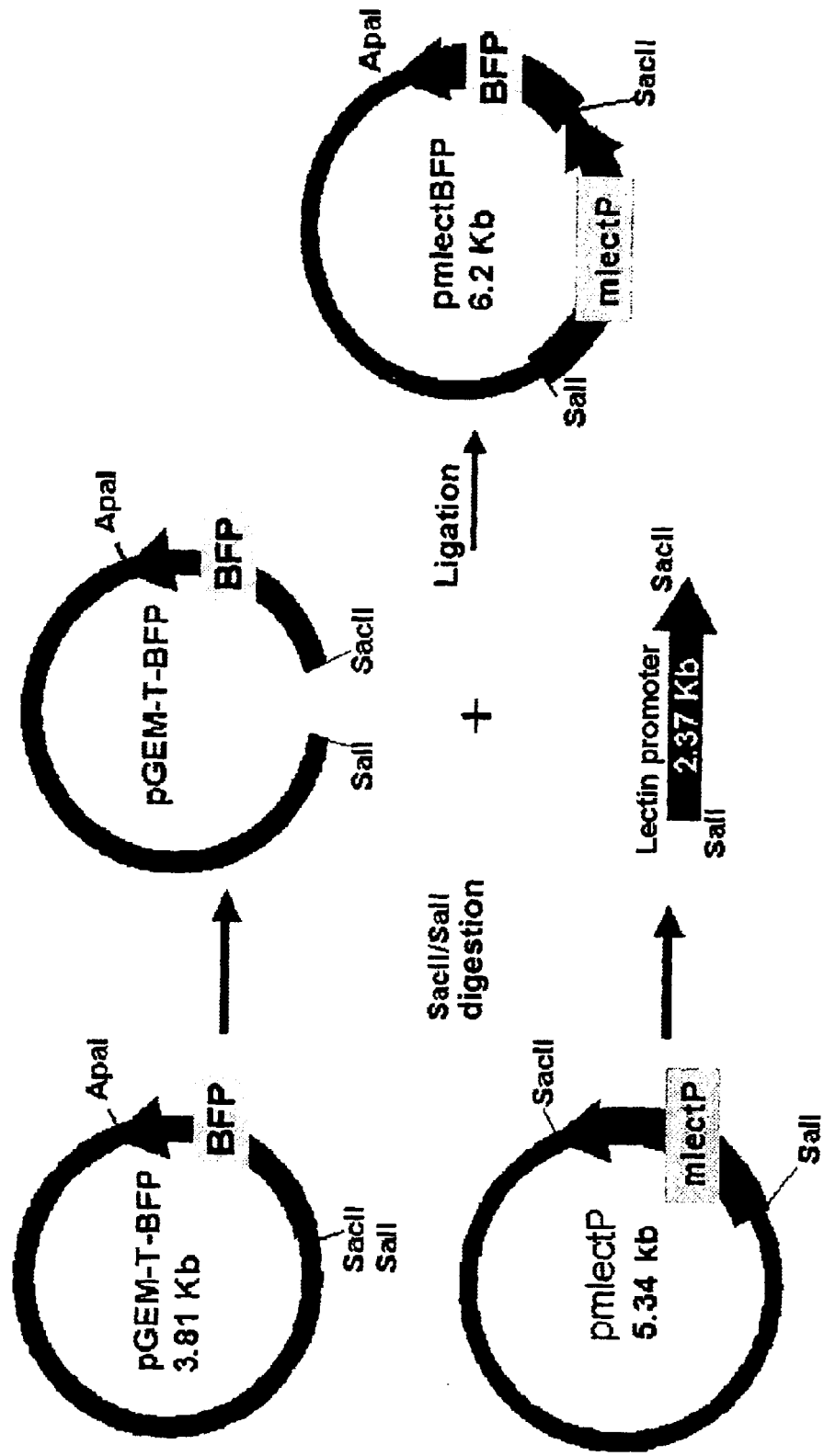
FIG. 3 is a diagram showing a manufacturing process of the expression vector of BFP containing the lectin gene regulation site of a mud loach (pmlectBFP)

(1) The commercial pQBI50 (Takira), an expression vector of BFP (blue fluorescence protein), was digested with Apa I and Sac II to obtain a BFP gene segment of 0.8 kb, which was then moved into a pGEM T easy vector at the site between Apa I and Sac II. The plasmid was digested with Sal I and Sac II, and the pmlectP was digested with Sal I and Sac II to obtain the lectin gene regulation site of a mud loach, which was then ligated with the plasmid segment to manufacture an expression vector pmlectBFP (6.2 kb) containing the lectin gene regulation site of a mud loach and the BFP gene. FIG. 3 is a diagram showing a manufacturing process of the expression vector of BFP containing the lectin gene regulation site of a mud loach (pmlectBFP).

Figure 4:
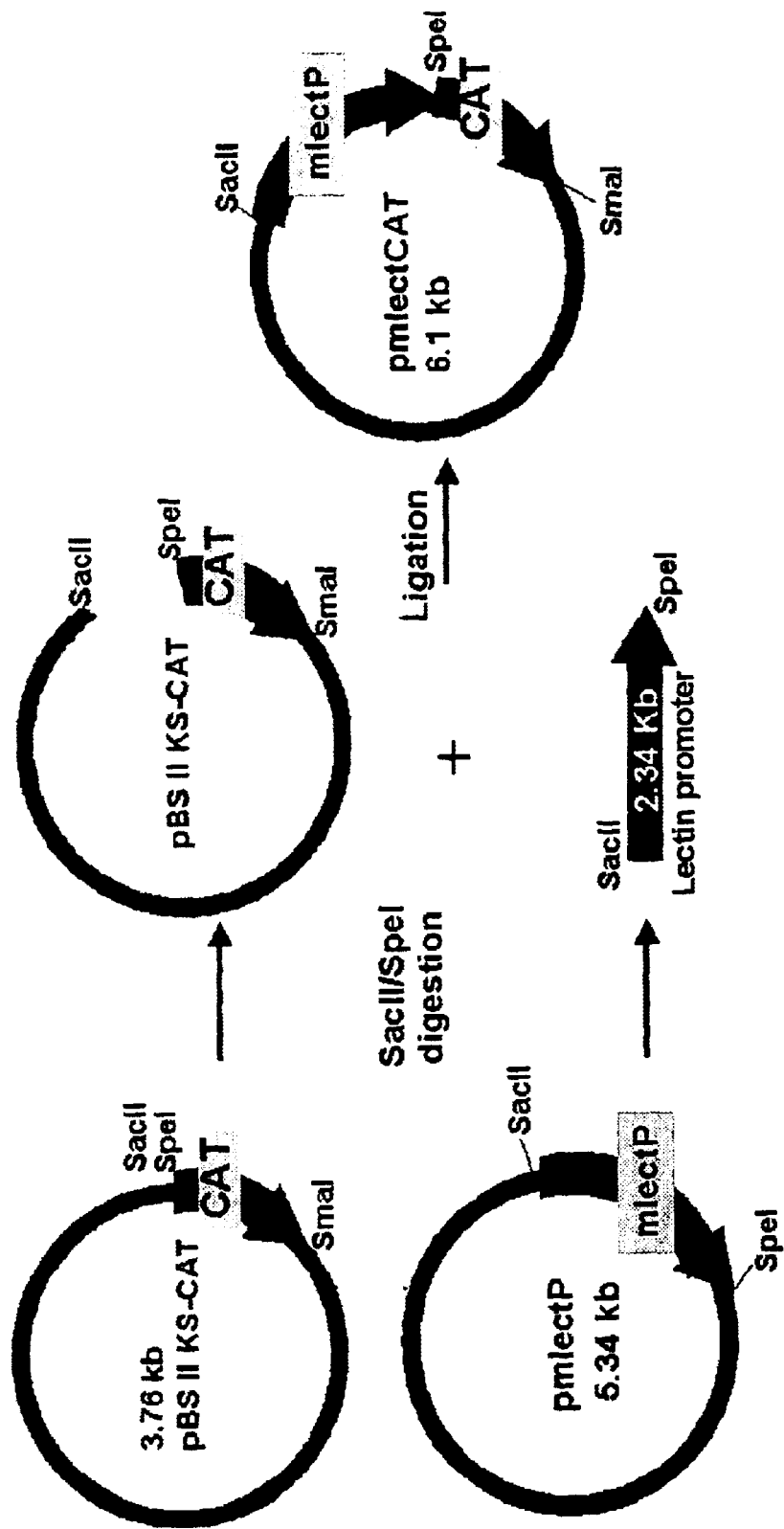
FIG. 4 is a diagram showing a manufacturing process of the expression vector of CAT containing the lectin gene regulation site of a mud loach (pmlectCAT)

(2) The plasmid pBS II KS containing a CAT (bacterial chloramphenicol acetyltransferase) gene was digested with Sac II and Spe I, and pmlectP was digested with the same enzymes to obtain the regulation site, which was then ligated with the plasmid segment to manufacture an expression vector pmlectCAT (6.1 kb) containing the lectin gene regulation site of a mud loach and the CAT gene. FIG. 4 is a diagram showing a manufacturing process of the expression vector of CAT containing the lectin gene regulation site of a mud loach (pmlectCAT).

3. Confirmation of the Ability of the Lectin Regulation Site to Induce Expression by Direct Injection into a Mud Loach Liver (1) The reporter expression vectors (pmlectBFP and pmlectCAT) were used to test the ability of the lectin regulation site of a mud loach to induce gene expression. The pmlectBFP plasrmid DNA was prepared at the concentration of 20 or 40 µg of DNA in 50 µl of phosphate buffer (PBS, pH 7.4). After its abdominal incision, 20 or 40 µg of pmlectBFP plasmid DNA (50 µl) was injected into liver tissues of mud loaches using 0.5 cc ¹⁄₂₆ G syringe. After the injection, the incised portion was restored with surgical thread. Four mud loaches were injected with each concentration of DNA, and four mud loaches of control group were injected with 50 µl of PBS. After the transfer, the mud loaches of the test and control groups were moved to an aquarium maintained at 25° C.

In the same way described above, the pmlectCAT gene was transferred into a mud loach liver to be used for analyzing the ability to induce expression.

(2) On four days after the injection, liver tissues were surgically removed from the mud loaches injected. In order to identify the plasmid to be injected into the liver tissue, small amount of tissue (10 mg) was collected from each sample and DNA was extracted from the samples for PCR analysis. As primers for the PCR, BFP 1F and BFP 1R were used for detecting the BFP gene, and CAT 1F and CAT 1R were used for detecting the CAT gene.

BFP 1F: 5'-GGC CAC AAG TTC TCT GTC AGT G-3' (SEQ. ID. No: 10)

BFP 1R: 5'-GGG CAG ATT GTG TGG ACA GG-3' (SEQ. ID. No: 11)

CAT 1F: 5'-CTA TAA CCA GAC CGT TCA GC-3' (SEQ. ID. No: 12)

CAT 1R: 5'-CGC CCC GCC CTG CCA CTC ATC GCA G-3' (SEQ. ID. No: 13)

Using each pair of primers, PCR were carried out under the following condition:
(Composition of solution for PCR)

| | |
|---|---|
| Distilled water | 28 µl |
| 10X PCR buffer with 15 mM MgCl$_2$ (Roche) | 5 µl |
| 10X dNTPs (each 2.5 mM) | 5 µl |
| 5 uM of forward primer | 5 µl |
| 5 uM of reverse primer | 5 µl |
| Taq DNA polymerase (Roche, 5 unit/µl) | 1 µl |
| Template gDNA (200 ng/µl) | 1 µl |

(Condition for PCR)
1 cycle: Initial denaturation at 94° C. for 2 minutes
30 cycles: Denaturation at 94° C. for 1 minute, annealing at 58° C. for 1 minute, and extension at 72° C. for 1 minute and 30 seconds.
1 cycle: Final extension at 72° C. for 3 minutes.

Figure 5A:
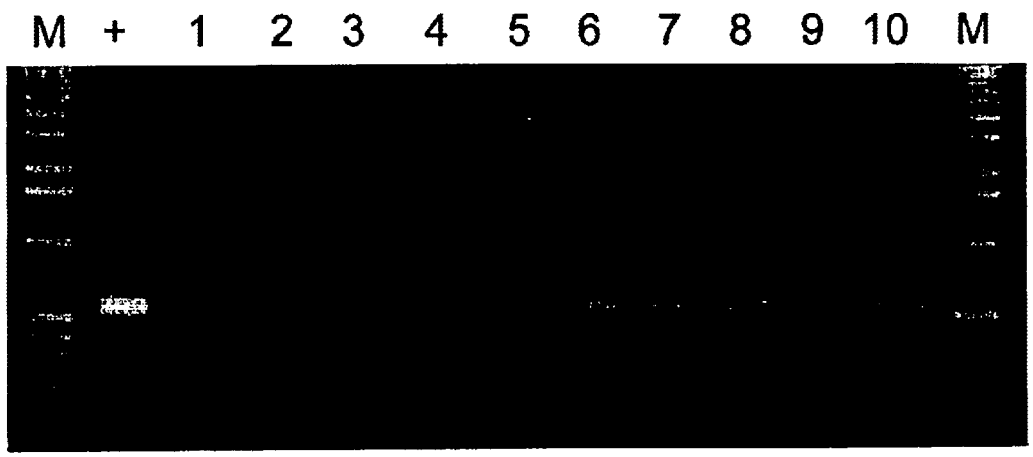
FIG. 5a is a photograph showing the PCR analysis of pmlectBFP that is transferred into a mud loach liver.
Figure 5B:
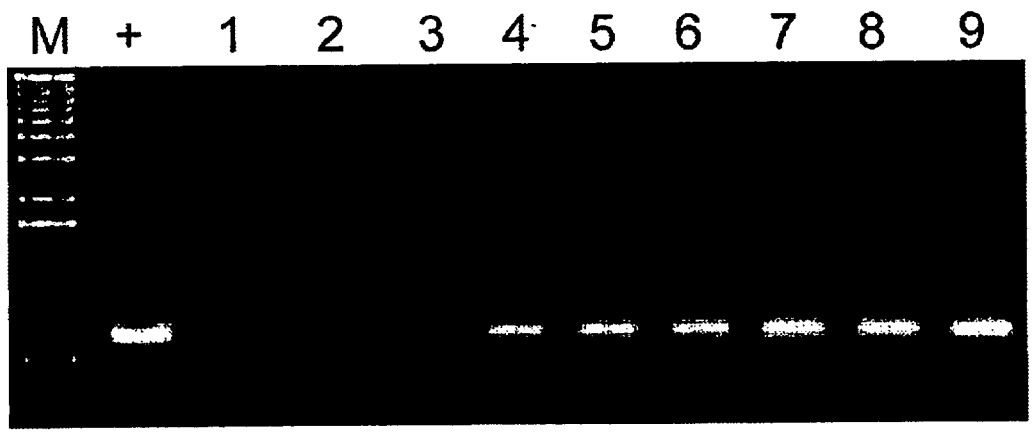
FIG. 5b is a photograph showing the PCR analysis of pmlectCAT that is transferred into a mud loach liver.

FIG. 5a is a photograph showing the PCR analysis of pmlectBFP that is transferred into a mud loach liver, and FIG. 5b is a photograph showing the PCR anaaysis of pmlectCAT that is transferred into a mud loach liver. In FIG. 5a M is 1 kb ladder (Gibco BRL), lanes 1~3 indicate control tissues injected with PBS alone, lanes 4~6 indicate tissues injected with 20 µg of pmlectBFP, and lanes 7~10 indicate tissues injected with 40 µg of pmlectBFP. In FIG. 5b, M is 1 kb ladder (Gibco BRL), lanes 1~3 indicate control tissues injected with PBS alone, lanes 4~6 indicate tissues injected with 20 µg of pmlectCAT, and lanes 7~9 indicate tissues injected with 40 µg of pmlectCAT. As shown in FIGS. 5a and 5b, PCR products amplified from the BFP and CAT genes are detected in all tissues injected with the plasmid DNA, which indicates successful gene transfer.

(3) To identify the synthesis of a BFP and CAT mRNA, total RNA was extracted fom half of the liver tissue (about 0.2 g) and RT-PCR was carried out. TriPure isolation kit (Roche) was used to separate the total RNA from the tissues. 1 µg of the RNA was treated with 10 units of DNase I (Promega) at 37° C. for 1 hour to remove the residual DNA contaminants in separated RNA samples. After the reaction was completed, the reactant was placed at 90° C. for 10 minutes to inactivate the DNase. 1 µg of the RNA was taken to carry out RT-PCR with one-step RT-PCR system (Roche). That is, reverse transcription was carried out at 50° C. for 1 hour, and then followed successively 30 cycles of PCR. The primers were the same as those to be used in the reaction described in (2).

Figure 6A:
FIG. 6a is a photograph showing the RT-PCR analysis of mRNA expressed from pmlectBFP that is transferred into a mud loach liver.
Figure 6B:
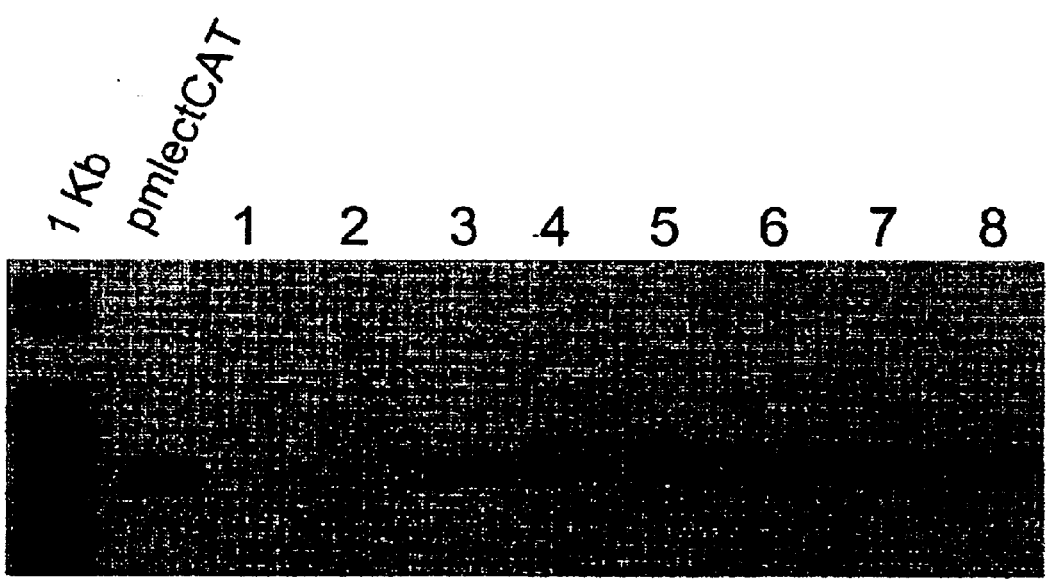
FIG. 6b is a photograph showing the RT-PC analysis of mRNA expressed from pmlectCAT that is transferred into a mud loach liver.

FIG. 6a is a photograph showing the RT-PCR analysis of mRNA expressed from pmlectBFP that is transferred into a mud loach liver; and FIG. 6b is a photograph showing the RT-PCR analysis of mRNA expressed from pmlectCAT that is transferred into a mud loach liver. In FIG. 6a, M is 1 kb ladder (Gibco BRL), lanes 1~3 indicate control tissues injected with PBS alone, lanes 4~6 indicate tissues injected with 20 µg of pmlectBFP, and lanes 7~10 indicate tissues injected with 40 µg of pmlectBFP. In FIG. 5b, M is 1 kb ladder (Gibco BRL), lanes 1 and 2 indicate control tissues injected with PBS alone, lanes 3~5 indicate tissues injected with 20 µg of pmlectCAT, and lanes 6~8 indicate tissues injected with 40 µg of pmlectCAT. As shown in FIGS. 6a and 6b, the BFP and CAT genes are successfully expressed in a liver. Accordingly, the ability of the lectin gene regulation site to induce the expression of the reporter gene has been confirmed by the mRNA lebel.

(4) The synthesis of the BFP and CAT protein was identified by the expression of pmlectBFP and pmlectl-CAT injected with liver tissues. The expression of pmlectBFP was identified on the tissues injected with pmlectBFP using a fluorometer. Specifically, 0.1 g of the liver tissue was homogenized in 2 ml of an extraction buffer (200 mM tris, pH 8.0, 0.1 mM PMSF), and then centrifuged at 5,000 rpm for 10 minutes to remove the unground tissue and ground dregs. The supernatant was taken and its intensity of fluorescence was determined at 460 nm.

Further, CAT-ELISA was carried out on the liver tissue injected with pmlectCAT to identify the expression of pmlectCAT. Specifically, 0. 1 g of the liver tissue was homogenized in the above-mentioned extraction buffer, and then centrifuged. The supernatant was taken and ELISA was carried out. In the ELISA, CAT-ELISA kit (Roche) containing a polyclonal horseradish CAT-antibody was used. After the completion of reaction, a microwell plate reader was used at 405 nm to detect the expression of the CAT protein.

FIG. 7 is a graph showing the expressions of pmlectBFP and pmlectCAT that are transferred into a mud loach liver. As shown in FIG. 7, both groups injected with BFP and CAT exhibit significant expression of the BFP and CAT protein. Accordingly, the lectin gene regulation site of a mud loach is considered to induce effectively the expression of a foreign gene in a mud loach liver.

EXAMPLE 2

Figure 8:
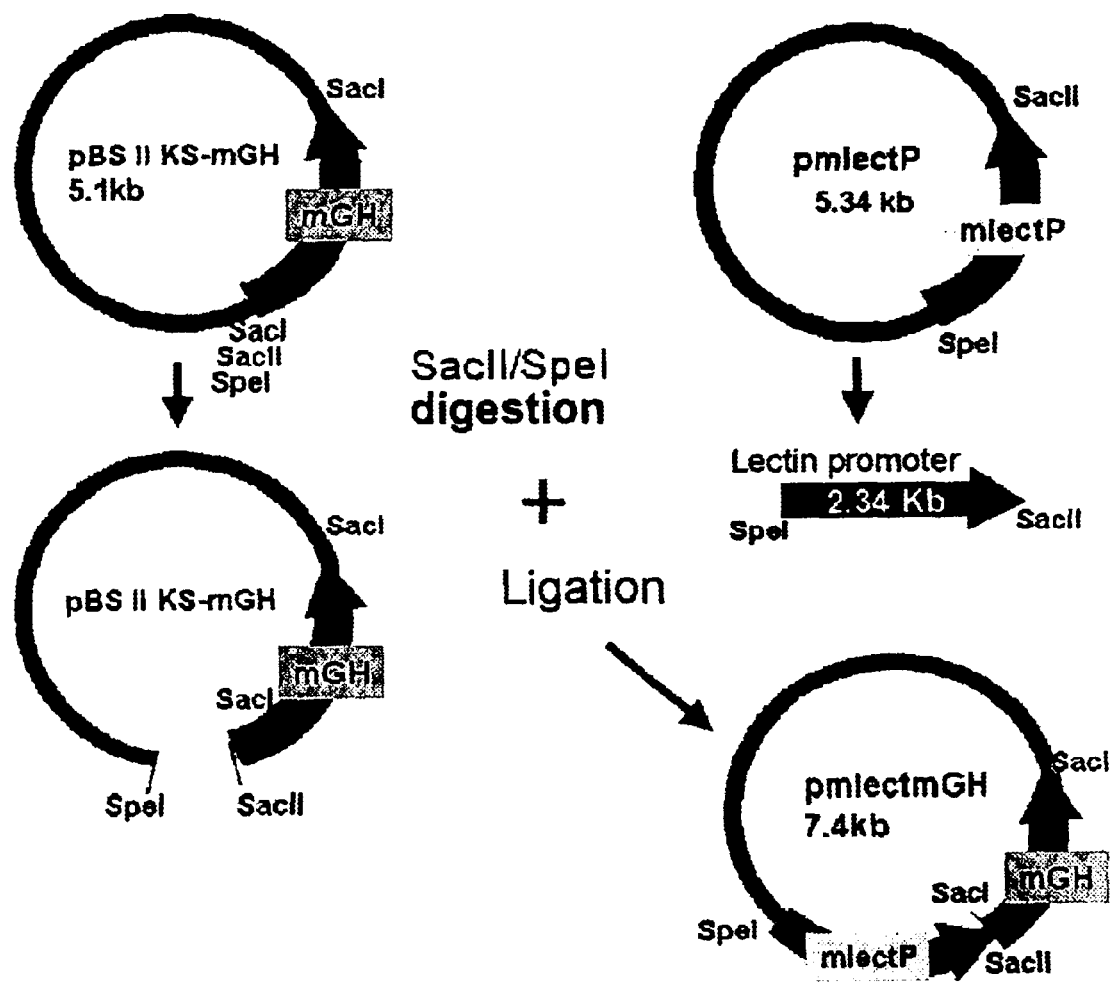
FIG. 8 is a diagram showing a manufacturing process of the expression vector of a mud loach growth hormone gene containing the lectin gene regulation site of a mud loach (pmlectmGH)

Manufacture of an Expression Vector of a Growth Hormone Gene Containing the Lectin Gene Regulation Site of a Mud Loach 1. Manufacture of an Expression Vector of a Mud Loach Growth Hormone Gene Containing the Lectin Gene Regulation Site of a Mud Loach The above-mentioned plasmid, pmlectP was digested with Sac II and Spe I to recover a lectin regulation site of 2.3 kb, and pBS II KS plasmid (pmlGH) containing a mud loach growth hormone gene was also digested with Sac II and Spe I . Both digested products were ligated to manufacture an expression vector of a mud loach growth hormone gene containing the lectin gene regulation site of a mud loach of 7.4 kb (pmlectmGH). FIG. 8 is a diagram showing a manufacturing process of the expression vector of a mud loach growth hormone gene containing the lectin gene regulation site of a mud loach (pmlectmGH).

The plasmid, pmlectmGH was introduced into E. coli XL1-Blue MRF' and deposited with the KCTC as accession number KCTC 10126BP on Nov. 22, 2001.

2. Manufacture of an Expression Vector of a Carp Growth Hormone Gene Containing the Lectin Gene Regulation Site of a Mud Loach (1) In order to manufacture an expression vector of a carp growth hormone gene containing the lectin gene regulation site of a mud loach, a carp growth hormone gene was separated from a carp genomic DNA by PCR. Based on the reported information of a carp growth hormone gene sequence, a forward primer (cGH 1F) and reverse primer (cGH 1R) were synthesized as follows. The primer cGH 1F was synthesized with recognition site for Sac II at the 5'-end for easy cloning.
cGH 1F: 5'-CCG CGG ACA AAC ATT CAC AAG CTC TTA ACT AAG-3' (Sac II) (SEQ. ID. No: 14)
cGH 1R: 5'-TTC TCT ATT AAA GTT TTA AAT TGC ATC CA-3' (SEQ. ID. No: 15)

Using the pair of primers, PCR was carried out under the following condition:
(Composition of solution for PCR)

| Distilled water | 28 µl |
| 10X PCR buffer with 15 mM MgCl₂ (Roche) | 5 µl |
| 10X dNTPs (each 2.5 mM) | 5 µl |
| 5 uM of forward primer cGH 1F | 5 µl |
| 5 uM of reverse primer cGH 1R | 5 µl |
| Taq DNA polymerase (Roche, 5 unit/µl) | 1 µl |
| Template DNA (1 µg/µl) | 1 µl |

(Condition for PCR)
1 cycle: Initial denaturation at 94° C. for 2 minutes
30 cycles: Denaturation at 94° C. for 1 minute, annealing at 58° C. for 1 minute, and extension at 72° C. for 1 minute and 30 seconds.
1 cycle: Final extension at 72° C. for 5 minutes.

Figure 9:
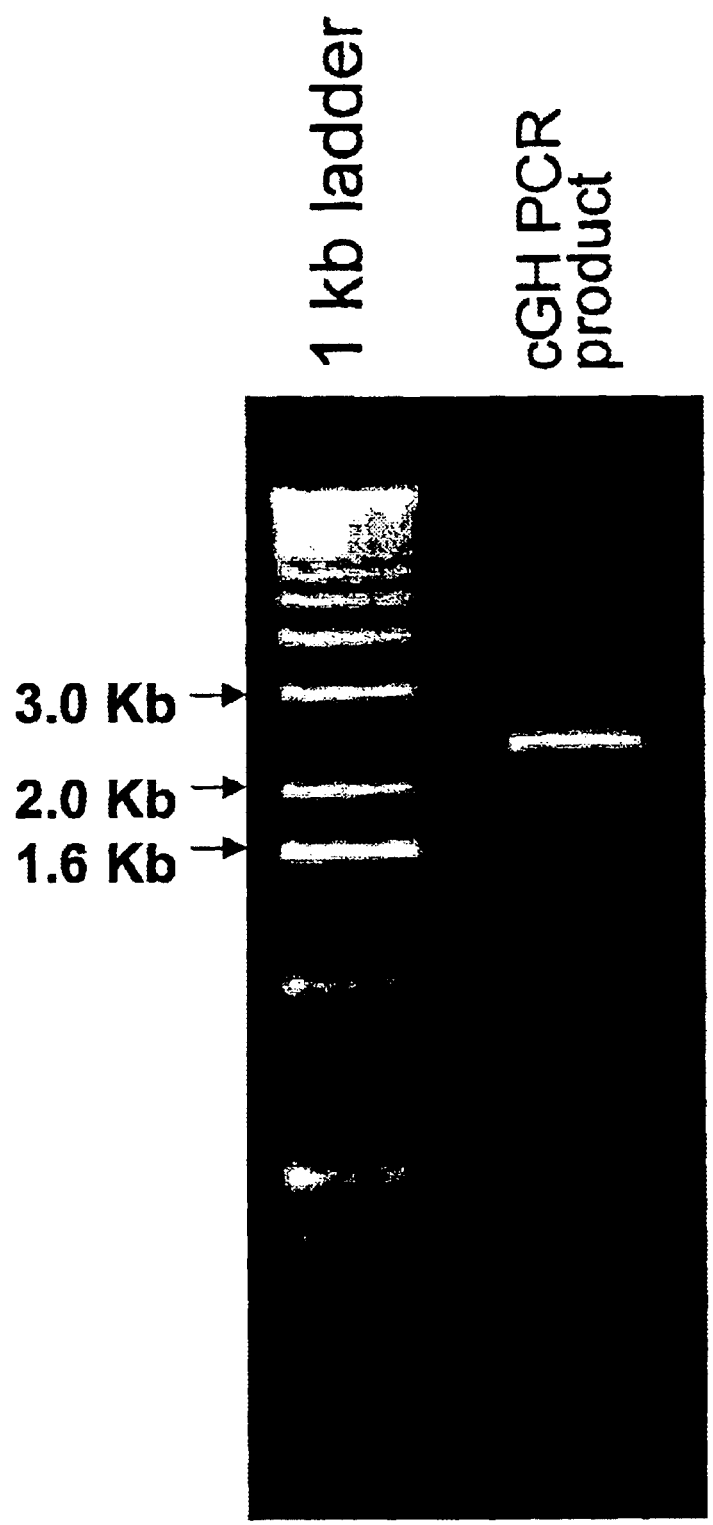
FIG. 9 is a photograph showing the PCR isolation of the growth hormone gene from a carp gDNA.

The carp growth hormone gene segment of 2.4 kb obtained by PCR was cloned into pGEM-T easy vector (Promega) by TA cloning to make pGEMcGH. FIG. 9 is a photograph showing the PCR isolation of the growth hormone gene from a carp gDNA. The DNA sequence of the PCR product cloned to pGEM-T easy vector was analyzed to confirm the correct amplification of a carp growth hormone gene.

Figure 10:
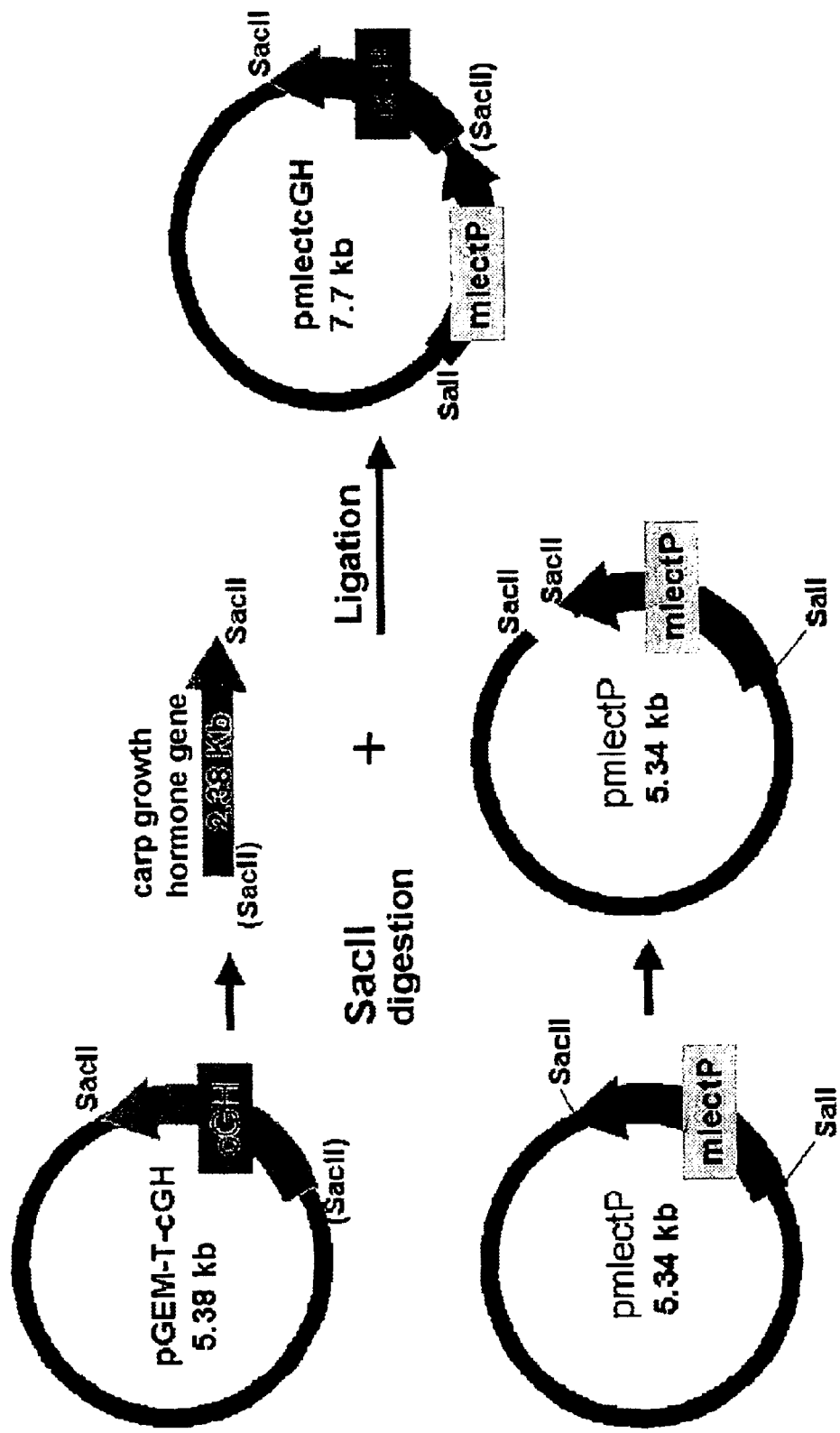
FIG. 10 is a diagram showing a manufacturing process of the expression vector of a carp growth hormone gene containing the lectin gene regulation site of a mud loach (pmlectcGH)

(2) The plasmid pGEMcGH containing a carp growth hormone gene was digested with Sac II to obtain a carp growth hormone gene of 2.4 kb, and pmlectP was also digested with the same restriction enzyme. Both digested products were ligated to manufacture an expression vector of a carp growth hormone gene containing the lectin gene regulation site of a mud loach of 7.7 kb (pmlectcGH). FIG. 10 is a diagram showing a manufacturing process of the expression vector of a carp growth hormone gene containing the lectin gene regulation site of a mud loach (pmlectcGH).

The plasmid, pmlectcGH was introduced into *E. coli* XL1-Blue MRF' and deposited with the KCTC as accession number KCTC 10125BP on Nov. 22, 2001.

EXAMPLE 3

Production of a Fast-gowing Transgenic Mud Loach and Carp

1. Production of a Fast-growing Transgenic Mud Loach

The expression vector of a mud loach growth hormone gene containing the lectin gene regulation site of a mud loach, pmlectmGH was micro-injected into fertilized eggs of a mud loach to confirm its ability to induce a fast-growing character.

(1) For micro-injection, pmlectmGH was purified and resuspended in a micro-injection buffer (10 mM Tris-HCl, pH 8.0; 0.1 mM EDTA, pH 8.0; 0.05% phenol red) at 100 µg/ml.

Mature female and male mud loaches were intraperitoneally injected with 6~8 IU/g of HCG (human chorionic gonadotropin) and placed at 25° C for 12 hours. After 12 hours, testis was extracted from the male mud loach with abdominal incision, cut and diluted to 1×10⁸ cells/ml in 0.85% NaCl solution to be placed at 4° C. Eggs were collected from the female mud loach under abdominal pressure. 1000 eggs were mixed with 300 µl of the diluted semen solution and the mixture was added with 1 ml of water at 25° C. to be fertilized. The fertilized eggs were washed twice with 50 ml of water at 25° C. and moved into an aquarium at 25° C. When the fertilized eggs began to cleavage and came to the first stage, the temperature of water was lowered to 12° C. to defer the cleavage and the prepared buffer solution containing pmlectmGH was micro-injected into the fertilized eggs. The micro-injected eggs were moved into an aquarium at 25° C. to be hatched.

(2) The hatched mud loaches were raised for 2 months and the mud loaches transformed with pmlectmGH were collected from all the 2 month-old mud loaches through PCR analysis. The primers for the PCR analysis were the forward primer lectP 2FW complementary to the mud loach lectin promoter and the reverse primer mlGH 3R complementary to the mud loach growth hormone gene.

lecP 2FW: 5'-GTT ATG GAG TCC CTC CCA C-3' (SEQ. ID. No: 16)

mlGH 3R: 5'-CAG CCA GCT GGT GCA GGT G-3' (SEQ. ID. No: 17)

Using the pair of primers, PCR was carried out under the following condition:
(Composition of solution for PCR)

| Distilled water | 28 µl |
| 10X PCR buffer with 15 mM MgCl₂ (Roche) | 5 µl |
| 10X dNTPs (each 2.5 mM) | 5 µl |
| 5 uM of forward primer lecP 2F | 5 µl |
| 5 uM of reverse primer mlGH 3R | 5 µl |
| Taq DNA polymerase (Roche, 5 unit/µl) | 1 µl |
| Template DNA (1 µg/µl) | 1 µl |

(Condition for PCR)
1 cycle: Initial denaturation at 94° C. for 2 minutes
30 cycles: Denaturation at 94° C. for 1 minute, annealing at 58° C. for 1 minute, and extension at 72° C. for 1 minute and 30 seconds.
1 cycle: Final extension at 72° C. for 5 minutes.

Table 1 shows the distribution of body weights in the group of mud loaches injected with pmlectmGH and the control group of mud loaches at two months after being hatched.

TABLE 1

| | Number of mud loaches | |
| --- | --- | --- |
| Body Weight | Non-injected | PmlectmGH-injected |
| 0.0–1.0 | 144 | 78 |
| 1.1–2.0 | 221 | 138 |
| 2.1–3.0 | 365 | 209 |
| 3.1–4.0 | 109 | 121 |
| 4.1–5.0 | 12 | 38 |
| 5.1–6.0 | 0 | 16 |
| 6.1–7.0 | 0 | 96 |
| 7.1–8.0 | 0 | 11 |
| 8.1–9.0 | 0 | 14 |
| 9.1–10.0 | 0 | 18 |
| 10.1–12.0 | 0 | 15 |
| 12.1–14.0 | 0 | 24 |
| 14.1–16.0 | 0 | 18 |
| 16.1–18.0 | 0 | 1 |
| 18.1–20.0 | 0 | 1 |
| 20.1–22.0 | 0 | 0 |
| 22.1–24.0 | 0 | 1 |
| 24.1–26.0 | 0 | 0 |
| 26.1–28.0 | 0 | 0 |
| 28.1–30.0 | 0 | 0 |

TABLE 1-continued

| | Number of mud loaches | |
|---|---|---|
| Body Weight | Non-injected | PmlectmGH-injected |
| 30.1–32.0 | 0 | 0 |
| 32.1–34.0 | 0 | 0 |
| 34.1– | 0 | 0 |
| Total | 851 | 799 |

As shown in Table 1, the control group represents a typical normal distribution while the pmlectmGH-injected group has some population having heavy weights deviated from a normal distribution. Most of the mud loaches having heavy weight are found to be a transgenic population, which explains the accelerated growth due to the expression vector of a growth hormone gene containing the lectin gene regulation site of a mud loach according to the present invention.

Figure 11:
FIG. 11 is a photograph showing the pmlectmGH-transgenic mud loach of eight months old compared with its normal mud loach sibling.

Further, the transgenic mud loaches and control group of two months old were carried out a fluorescent marking of different colors (Northwest Marine Technology Inc., USA) and were taken to the same aquarium at 25° C. The mud loaches were fed with commercial carp fodder (39% protein) and the increase of their body weight were measured until nine months after being hatched. As a result, the tansgenic group shows an accelerated increase of body weight seven times as high as the control group. Specifically, at the end of the experiment the mean body weight of the control group was 12±2 g while that of the pmlectmGH-injected group was 89±14 g. FIG. 11 is a photograph showing the pmlectmGH-transgenic mud loach of eight months old compared with its normal mud loach sibling.

(3) Among the first generation of the transgenic mud loaches, seven males were selected by random sampling to find the transfer of the injected gene to the next generation. Specifically, after an artificial fertilization of the sperm samples collected from seven transgenic males and two normal males according to the process described in (1) and the eggs obtained from normal female mud loaches, the fertilization rate, hatching rate and early survival rate were measured. As a result, the eggsfertilized with the transgenic males show 89~94% of fertilization rate, 83~90% of hatching rate and 82~91% of early survival rate, which has no difference with those of the control group (p>0.05). PCR was carried out to 20~30 newly hatched mud loaches randomly collected to measure the incidence of transgenic progeny. Table 2 shows the aspect of gene transfer in pmlectmGH from the transgenic F0 mud loaches to the F1 generation. In Table 2, the early survival means the survival rate of newly hatched fishes until the vitelline imbibition.

TABLE 2

| Experimental male | Fertilization rate (%) | Hatching success (%) | Early survival (%) | Incidence of Transgenic progeny (%) |
|---|---|---|---|---|
| CON M1 | 91 ± 4 | 85 ± 6 | 82 ± 4 | 0 |
| CON M2 | 92 ± 3 | 89 ± 4 | 88 ± 3 | 0 |
| TGM#1 | 93 ± 5 | 84 ± 3 | 84 ± 6 | 27 ± 4 |
| TGM#2 | 89 ± 4 | 83 ± 5 | 88 ± 3 | 38 ± 4 |
| TGM#3 | 92 ± 3 | 90 ± 5 | 82 ± 5 | 32 ± 2 |
| TGM#4 | 94 ± 3 | 89 ± 3 | 90 ± 4 | 42 ± 1 |
| TGM#5 | 90 ± 5 | 86 ± 6 | 91 ± 5 | 26 ± 4 |

As shown in Table 2, five of the seven trrnsgenic mud loaches injected with pmlectmGH transferred the genes to the next generation and the incidences of transgenic progeny had various values from 26% to 42%, which has shown mosaic form of the first F0 transgenic mud loaches.

(4) Among the six F1 populations produced by the process of (2), 30% high-ranking mud loaches were selected separately at one, two and three weeks after being hatched to collect 60~70 fast-growing transgenic mud loaches by each group. Examination of the growth of each system by two repetitions (22 mud loaches per repetition) showed that all the six transgenic populations came to a commercially available size (10~12 g) within 2~3 months while the control groups came to the commercially available size by 9 months. At the time stage when the transgenic groups come to the commercially available size, the six transgenic populations showed 6~10 times accelerated growth rate compared with the control groups.

(5) For three systems of the transgenic F1 mud loaches, feed conversion efficiency was measured and compared with control groups. Eighteen transgenic mud loaches and the same number of normal mud loaches were raised in three repetitive 200 l aquariums fed with commercial carp fodder. To calculate the feed conversion efficiency, the increment of body weight (g) per the amount of fodder supplied to the groups was measured for eight weeks. The temperature of the aquarium was maintained at 25° C. and a circulating filtration system was used to supply the same quality of water to all the repeating aquariums. The fodder was given ten times a day from nine a.m. to seven p.m. with satiety.

Figure 12:
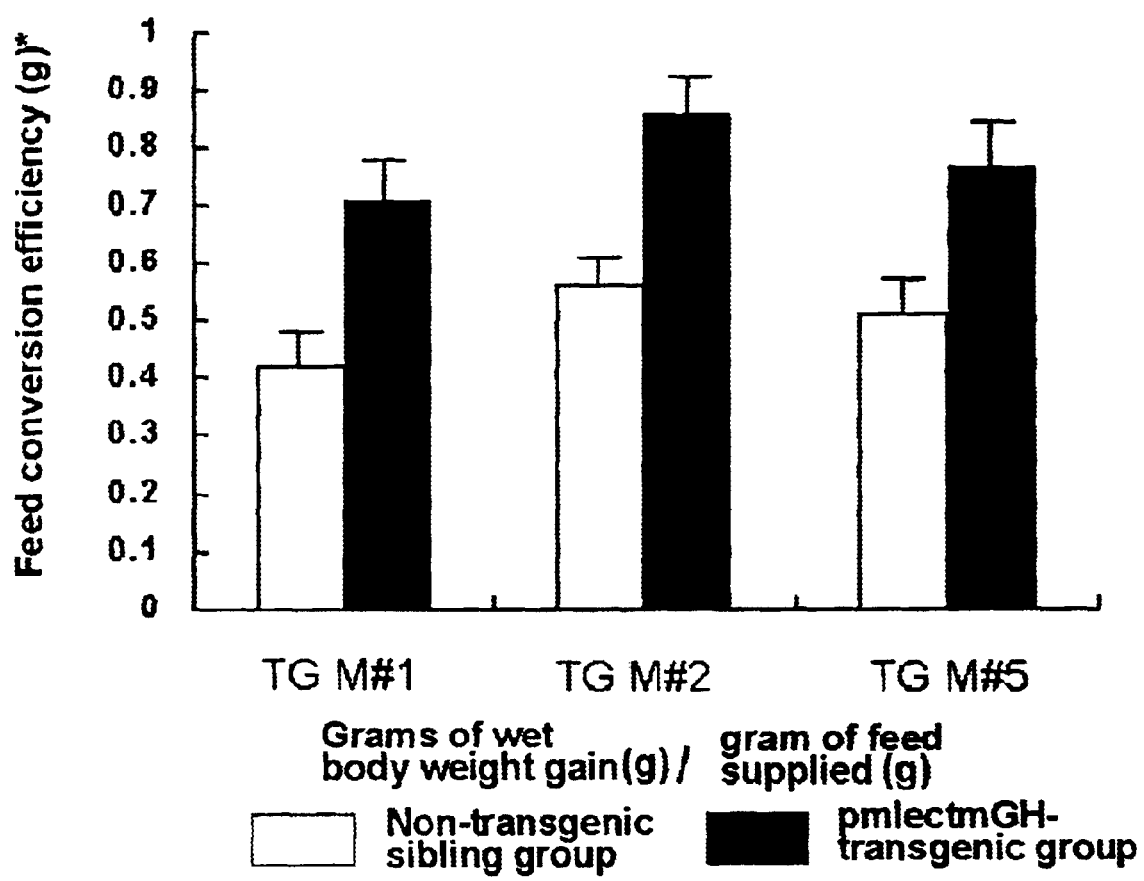
FIG. 12 is a graph showing the feed conversion efficiency of the pmlectmGH-transgenic mud loach and non-transgenic sibling group.

FIG. 12 is a graph showing the feed conversion efficiency of the pmlectmGH-transgenic mud loach and non-transgenic sibling group. As shown in FIG. 12, the feed conversion efficiencies of transgenic mud loaches appears to be about 1.5 times higher than those of non-tramgenic sibling groups, which shows the effect of the present invention.

2. Production of a Fast-growing Transgenic Carp

In order for the lectin gene promoter of a mud loach to work on other fishes such as carp, the expression vector containing the lectin gene promoter of a mud loach with a carp growth hormone gene (pmlectcGH) was injected into fertilized eggs of a carp. The examples and analyses are as follows.

(1) Artificial fertilization of eggs and sperms obtained from a mature female and male carp was carried out as follows: 500 μl of carp semen diluted in 0.85% NaCl at the ratio of 1:5 was mixed with 500 carp eggs and the mixture was added with 10 ml of water at 25° C. to be fertilized. The fertilized eggs were washed with 100 ml of water and moved into an aquarium at 25° C. When the developmental stage came to the first stage, the fertilized eggs were moved into an aquarium maintained at 12° C. to defer the cleavage and the microinjection of pmlectcGH was carried out. The microinjection was carried out according to the same process as described in the production of a fast-growing mud loach.

(2) At 1 month after being hatched, the distribution of body weight was examined between the injected groups and control groups. Among the injected groups, the population deviated from a normal distribution were collected and PCR analysis was carried out to confirm their transformation. The primers for the PCR analysis were the forward primer lectP 2FW complementary to the mud loach lectin promoter and the reverse primer cGH 2R complementary to the carp growth hormone gene.

lecP 2FW: 5'-GTT ATG GAG TCC CTC CCA C-3' (SEQ. ID. No: 16)
cGH 2R: 5'-ACA ACA CCT GCA CCA GCT GGC TG-3' (SEQ. ID. No: 18)

Using the pair of primers, PCR was carried out under the following condition:

Composition of solution for PCR)

| | |
|---|---|
| Distilled water | 28 µl |
| 10X PCR buffer with 15 mM MgCl₂ (Roche) | 5 µl |
| 10X dNTPs (each 2.5 mM) | 5 µl |
| 5 uM of forward primer lecP 1F | 5 µl |
| 5 uM of reverse primer cGH 2R | 5 µl |
| Taq DNA polymerase (Roche, 5 unit/µl) | 1 µl |
| Template DNA (1 µg/µl) | 1 µl |

(Condition for PCR)
1 cycle: Initial denaturation at 94° C. for 2 minutes
30 cycles: Denaturation at 94° C. for 1 minute, annealing at 58° C. for 1 minute, and extension at 72° C. for 1 minute and 30 seconds.
1 cycle: Final extension at 72° C for 5 minutes.

Figure 13:
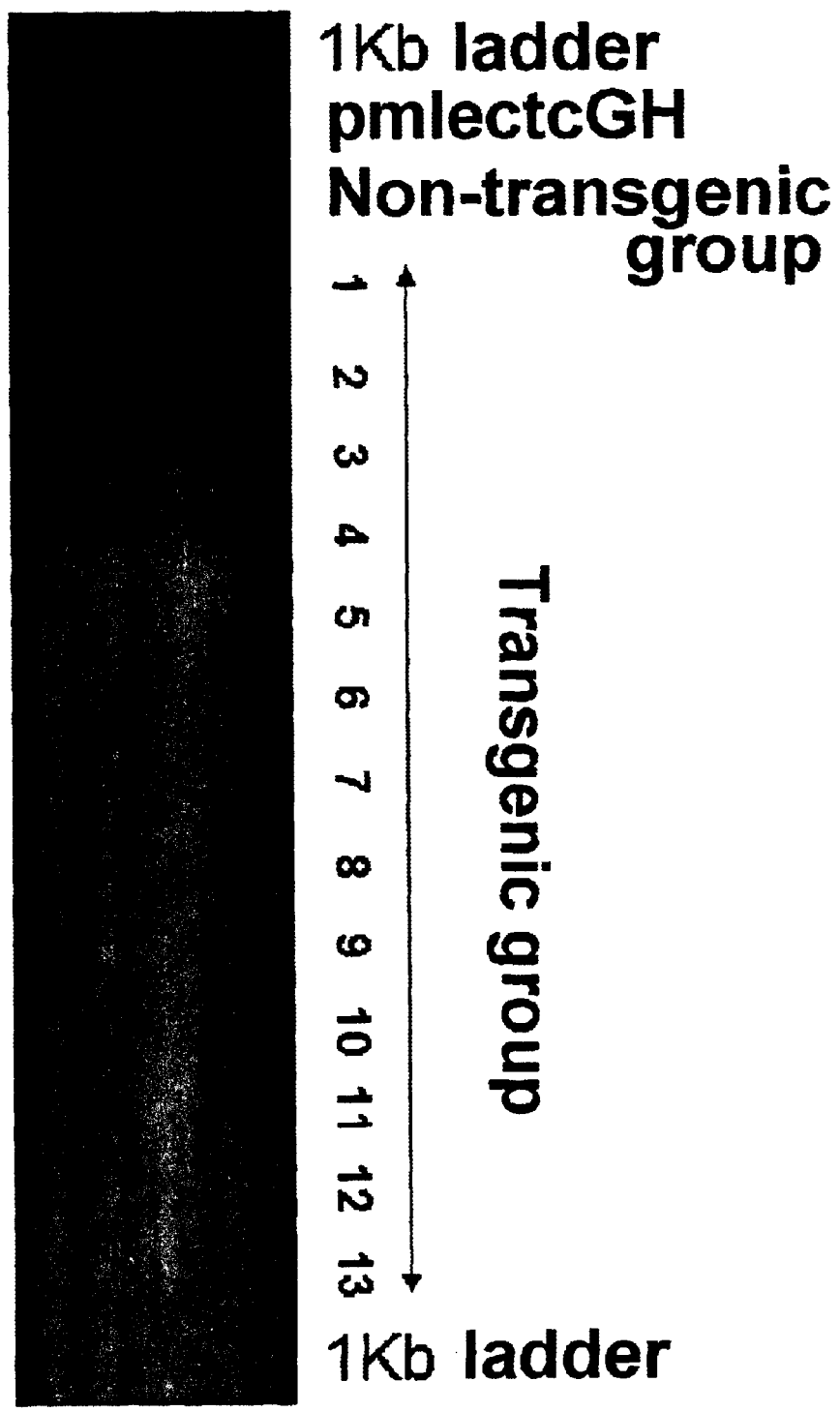
FIG. 13 is a photograph showing the PCR analysis of a fast-growing carp group that is deviated from a normal distribution in the pmlectcGH-transgenic group.

As a result, the incidence of the fast-growing individuals which laid outside a normal distribution of carp body weights was 23% (179/789) of total micro-injected groups. PCR analysis of the fast-growing population showed that 98% of them were transgenic carp contaniing pmlectcGH in their blood or fin, which indicated growth acceleration due to the micro-injection of the expression vector of growth hormone according to the present invention. FIG. 13 is a photograph showing the PCR analysis of a fast-growing carp group that is deviated from a normal distribution in the pmlectcGH-transgenic group.

Figure 14:
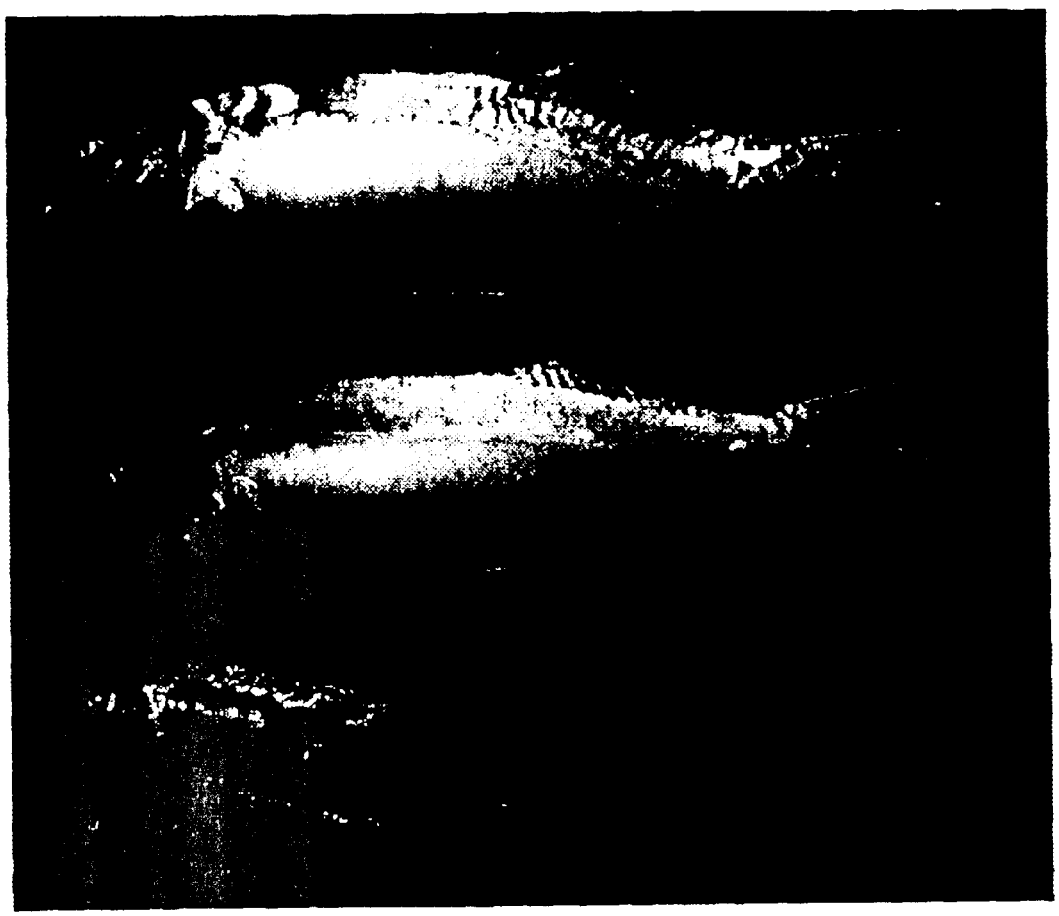
FIG. 14 is a photograph showing the pmlectcGH-transgenic carp of seven months old compared with its normal carp sibling.
Figure 15:
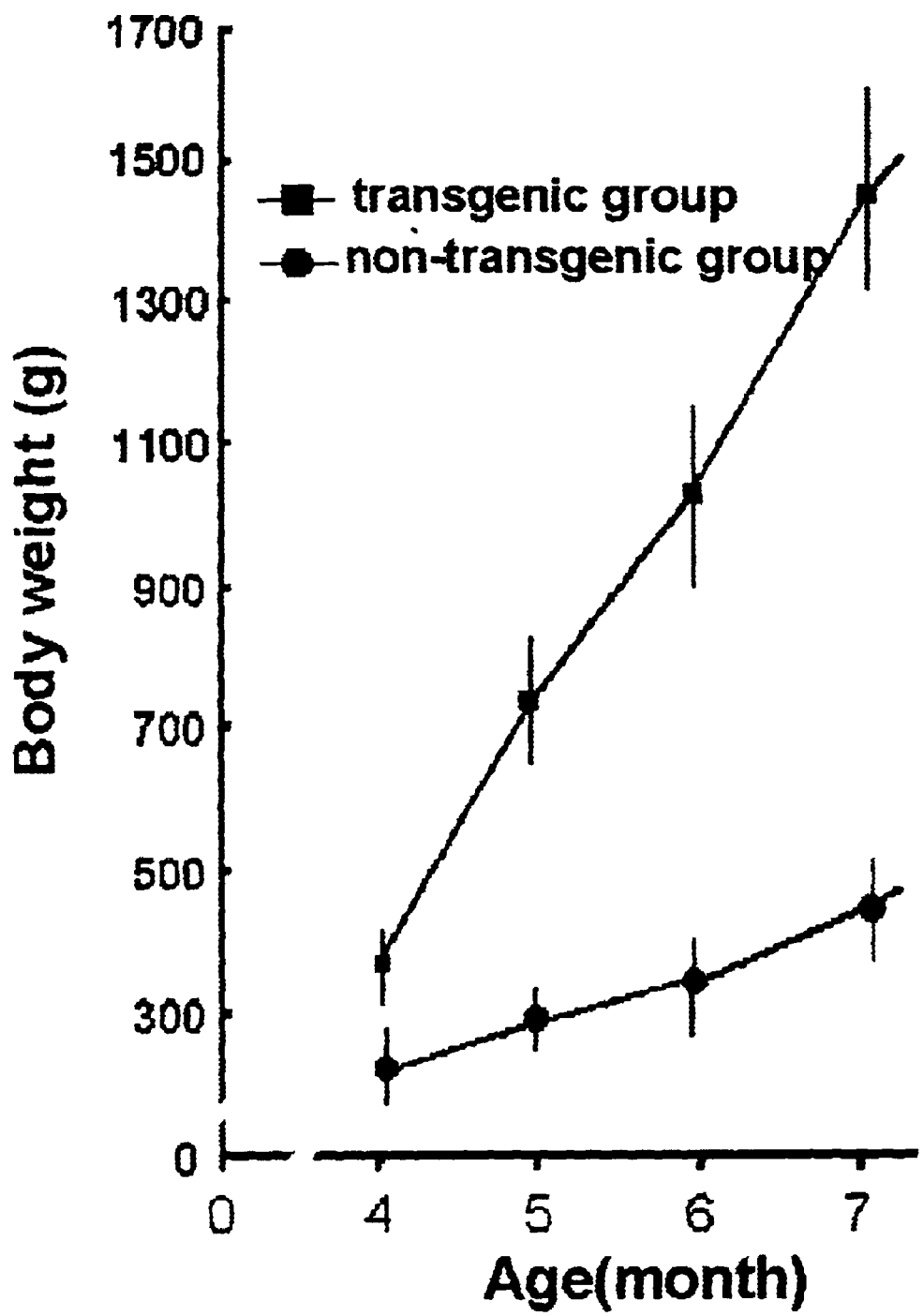
FIG. 15 is a graph showing the growth curve of the pmlectcGH-transgenic carp group and non-transgenic sibling group.

(3) Thirty transgenic carp were randomly selected from the F0 generation at four months after hatch, and each 10 transgenic individuals was allocated into one of triplicate tanks (2×4 m²) with same number of non-transgenic control fish. Communal culture was performed to examine the growth of transgenic and non-trnnsgenic fish until seven months post hatch. Similar quality of water was supplied using water-recirculating system and the water temperature was 25° C. through the growth trial. Cumulative survival rate of the two groups showed no significant difference and both groups showed not less than 95% survival rates (p>0.05). The transgenic carp groups showed significant increase of body weight, which were observed in 30 days after the beginning of the experiment. At the last seventh month, there was at least 3 times of difference in mean body weight between the two groups. FIG. 14 is a photograph showing the pmlectcGH-transgenic carp of seven months old compared with its normal carp sibling, and FIG. 15 is a graph showing the growth curve of the pmlectcGH-transgenic carp group and non-transgenic sibling group.

As described above, the expression vector containing the lectin gene regulation site of a mud loach is available to express a wide variety of proteins in a mud loach or carp body. Especially, the expression vector of growth hormone gene containing the lectin gene regulation site of a mud loach is useful to produce a transgenic mud loach or carp which shows a stabilized improvement of growth rate without such adverse effect as excessive growth acceleration and has a significantly improved feed conversion efficiency, therefore, to improving the culturing productivity.

What is claimed is:

1. An isolated polynucleotide comprising the nucleic acid sequence of SEQ ID NO: 1.

2. An expression vector comprising a lectin gene regulation site of *Misgurnus mizolepis,* wherein said vector is pmlectP (KCTC 10124BP).

* * * * *

SEQUENCE LISTING

<160> NUMBER OF SEQ ID NOS: 18

<210> SEQ ID NO 1
<211> LENGTH: 2329
<212> TYPE: DNA
<213> ORGANISM: Misgurnus mizolepis

<400> SEQUENCE: 1

```
aagagtgtgg ctttctaccc agaacattcc gatgcgttcc gtctcgaata aacttgctcc      60
caaatttatt ggcccgtttt ctgttaccaa gatcattaat ccggtaacag tgcgtctgag     120
ccttcctccg gcgtacagga gggttcaccc tgtgttccac gtctccaata ttaaaccggt     180 gatttttttcc cgtcttaatc cgcctgcccc ggttcccccc ccgcctcgtc tcgttaatgg     240
ggaaccgact tattcggtta atcgtattct ggactccaga cggaggggac gcggatttca     300
gtacttggtg gattgggaag gttacggtcc ggaggagaga aggtgggttc ctgctcggga     360
catactggat caccgcctta tcgatgttta caatcaacag gtaaagcagg ctgggaacgt     420 caagggggcgt tcctagggga gggggtactg tcacggtagg aaatcctctg tttcctccgt     480
gtcatgtttg tgtgtgtgtg tgtttgttac tctctgctct gccatgtgct cgttaggctg     540
atgtcgctca cctgtgtgtt gattgcctcg ctccagctgc tcatcattac atctcctcca     600
taaatactca catgactctc tgttccctgc cagatgatca ctttctgttt ggtcctcgtg     660
ttgtgtggtt ctacgtctca gtcttggatt acgagttgca ttgtggattg tttattgtcg     720
```

-continued

```
tagtcgtctt cgtgtggatg ttccgtgtac agtctggatt caccactgct caccactcca      780
ccaacgccgc actcaataac cacctaccac cgtagtcctc gtcaccattg ccaacaacac      840
cggacatttc ctgcttgtgt catttctctc tttgtgttta taaataaaca ttgtgttttc      900
acctgcaatt gcttccgctc agttcgtgtc attacaagta cctcaaaata catattagta      960
tctcaaaggt acatattgct actaaatgtt tacacatctg tacctaatgg tccatacaat     1020 tacctttta aagggtgctg ccccagtgac agctagggta catattttga cttttttcta     1080
acaatgtagg tcctaaaggt acggtaggct aatctaccca aaattgtatt ctgttttgta     1140
ttcctgtagg taccaaacag aaacttaggg tacagcccca gtgacagaaa aggtacagtt     1200
ttgtacctta atttctgaca atgaacgata aacaagaata actaaaacac taccaaatga     1260
tactaaaaac gaaagcataa aaaagatgaa actaaaatg caagaaaag aaaactgaag      1320 tgactgagtt aaatttatgg cagaatgttt cctgtttctg ataagatgaa aaccttactt     1380
ctaataaccc aaataaccaa ataattatct gcaaacatta agaaactca gttatgcaat      1440 ctatggtaaa tagttactga agaatacac caatgccaag gttttggggc aagaggtttg      1500
tttacatgat atttactttt tgtgtggtca gatgagctgt ccggtggtgg gcccgtcggc     1560
catggttcag gcttttacgt gctgcaaatg ggaatgagtc aggttcagtt caacagcctt     1620
gaacacgaag tgatgtgaaa tgctgatcag ctgttcagct taaaaaagt tcatttgctg      1680 ccttaaaatc caactttaaa atattagttg acacaaacag ttttaaacag tttctcgttt     1740
tgagtcaact aatattttta agttgaatga actcaaaatt ttagtcgct ttttaagttg      1800 aaacatttct ttaccgttta tatcaagcag actgcaataa aactcttaca aaaatgcttc     1860
tttgcatgat cacacacatt aaagaaacac actaaaaata caaaaataaa caaatctata     1920
tatgcaatat atttatataa aatacttgca ataaacagta aaataacaaa atctaatgta     1980
aagacatgag tcaataaaaa tatgtaaaac atccataaat gtaaaatata ctgaaagaaa     2040
tgtgaacaca gaaaagtgtt catgtgtcag atcaggatgt ttattttgat aaccatcaca     2100
tttcatcata tattgtatac atatatacaa gttcatgata tccagattta cttttcttgt     2160
ttatgttatg gagtccctcc cactgaacaa agtataaaa gataggactc ctcattgacc      2220
atcacacaat ctacactgaa gttctgaaag tgaagatttg acaaaaaggt gagttttat      2280 aacattaact tcagcagtgt acatatgagt gcagatgtgt cacttttcc                 2329
```

<210> SEQ ID NO 2
<211> LENGTH: 7224
<212> TYPE: DNA
<213> ORGANISM: Misgurnus mizolepis
<220> FEATURE:
<221> NAME/KEY: CDS
<222> LOCATION: (2425)..(2487)
<221> NAME/KEY: CDS
<222> LOCATION: (2695)..(2778)
<221> NAME/KEY: CDS
<222> LOCATION: (2889)..(3014)
<221> NAME/KEY: CDS
<222> LOCATION: (3198)..(3311)
<221> NAME/KEY: CDS
<222> LOCATION: (3918)..(3986)

<400> SEQUENCE: 2

```
caggtgaggt cgcgcaccaa ggctaaggcc gatcgccacc agtcgaagcc tccccgttac       60
gtcgtcggtc aaagagtgtg gctttctacc cagaacattc cgatgcgttc cgtctcgaat      120
aaacttgctc ccaaatttat tggcccgttt tctgttacca agatcattaa tccggtaaca      180
```

-continued

```
gtgcgtctga gccttcctcc ggcgtacagg agggttcacc ctgtgttcca cgtctccaat      240
attaaaccgg tgattttttc ccgtcttaat ccgcctgccc cggttccccc cccgcctcgt      300
ctcgttaatg gggaaccgac ttattcggtt aatcgtattc tggactccag acggagggga      360
cgcggatttc agtacttggt ggattgggaa ggttacggtc cggaggagag aaggtgggtt      420
cctgctcggg acatactgga tcaccgcctt atcgatgttt acaatcaaca ggtaaagcag      480
gctgggaacg tcaaggggcg ttcctagggg aggggtact gtcacggtag gaaatcctct       540
gtttcctccg tgtcatgttt gtgtgtgtgt gtgtttgtta ctctctgctc tgccatgtgc      600
tcgttaggct gatgtcgctc acctgtgtgt tgattgcctc gctccagctg ctcatcatta      660
catctcctcc ataaatactc acatgactct ctgttccctg ccagatgatc actttctgtt      720
tggtcctcgt gttgtgtggt tctacgtctc agtcttggat tacgagttgc attgtggatt      780
gtttattgtc gtagtcgtct tcgtgtggat gttccgtgta cagtctggat tcaccactgc      840
tcaccactcc accaacgccg cactcaataa ccacctacca ccgtagtcct cgtcaccatt      900
gccaacaaca ccggacattt cctgcttgtg tcatttctct ctttgtgttt ataaataaac      960
attgtgtttt cacctgcaat tgcttccgct cagttcgtgt cattacaagt acctcaaaat     1020
acatattagt atctcaaagg tacatattgc tactaaatgt ttacacatct gtacctaatg     1080
gtccatacaa ttacctttt aaagggtgct gccccagtga cagctagggt acatattttg      1140
acttttttct aacaatgtag gtcctaaagg tacggtaggc taatctaccc aaaattgtat     1200
tctgttttgt attcctgtag gtaccaaaca gaaacttagg gtacagcccc agtgacagaa     1260
aaggtacagt tttgtacctt aatttctgac aatgaacgat aaacaagaat aactaaaaca     1320
ctaccaaatg atactaaaaa cgaaagcata aaaaagatga aaactaaaat gcaagaaaa     1380
gaaaactgaa gtgactgagt taaatttatg gcagaatgtt tcctgtttct gataagatga     1440
aaaccttact tctaataacc caaataacca aataattatc tgcaaacatt aaagaaactc     1500
agttatgcaa tctatggtaa atagttactg aaagaataca ccaatgccaa gttttttggg     1560
caagaggttt gtttacatga tatttacttt ttgtgtggtc agatgagctg tccggtggtg     1620
ggcccgtcgg ccatggttca ggcttttacg tgctgcaaat gggaatgagt caggttcagt     1680
tcaacagcct tgaacacgaa gtgatgtgaa atgctgatca gctgttcagc ttaaaaaaag     1740
ttcatttgct gccttaaaat ccaactttaa aatattagtt gacacaaaca gttttaaaca     1800
gtttctcgtt ttgagtcaac taatattttt aagttgaatg aactcaaaat tttaagtcgc     1860
tttttaagtt gaaacatttc tttaccgttt atatcaagca gactgcaata aaactcttac     1920
aaaaatgctt ctttgcatga tcacacacat taaagaaaca cactaaaaat acaaaaataa     1980
acaaatctat atatgcaata tatttatata aaatacttgc aataaacagt aaaataacaa     2040
aatctaatgt aaagacatga gtcaataaaa atatgtaaaa catccataaa tgtaaaatat     2100
actgaaagaa atgtgaacac agaaaagtgt tcatgtgtca gatcaggatg tttattttga     2160
taaccatcac atttcatcat atattgtata catatataca agttcatgat atccagattt     2220
acttttcttg tttatgttat ggagtccctc ccactgaaca aaagtataaa agataggact     2280
cctcattgac catcacacaa tctacactga agttctgaaa gtgaagattt gacaaaaagg     2340
tgagtttta taacattaac ttcagcagtg tacatatgag tgcagatgtg tcactttttcc     2400
tgttcattca ttttcagatt catc        atg gca gtc atg aga gct ctt gtg    2448
                                  Met Ala Val Met Arg Ala Leu Val
                                   1               5
```

```
                                                                -continued ctt ctt ttc ttg gtc ttt tct gtt gag agt gca cca ggt         aac    2490
Leu Leu Phe Leu Val Phe Ser Val Glu Ser Ala Pro Gly
    10              15                  20 caagacgttt acaagattga ccaaaccctg ttaccaatat tccagattaa attcccataa   2550
aattgtgttt tccataaaac ttgttaaaca ttataaacat catgaaagga tgtcaacaga   2610
agcaacattt aaagcactta tagacagaaa cataaaacta ataatgtgac tttatattac   2670
taatatttta atcactgtat agct       cat cgc tgc cca cat gga tgg aca   2718
                                 His Arg Cys Pro His Gly Trp Thr
                                   1               5 ccc ttt ggt gtg caa tgc tac aaa ttc ttc tct cag tca gtt gac tgg   2766
Pro Phe Gly Val Gln Cys Tyr Lys Phe Phe Ser Gln Ser Val Asp Trp
    10              15                  20 atc aca gct gag    gt actgttattc agttattcaa attgttgaat aagaatactc   2820
Ile Thr Ala Glu
 25 aatgtcatga tccaagctga aacagattag atttttatatt tgcaataaaa taatctctct   2880 ctctttag    aaa aac tgt caa tct att gat gct aat ctt gca tct gtg cgc   2930
            Lys Asn Cys Gln Ser Ile Asp Ala Asn Leu Ala Ser Val Arg
              1               5                   10 agt aca atg gaa cac aac ttt ctc ctg agt ctg att gtg tct gct aac   2978
Ser Thr Met Glu His Asn Phe Leu Leu Ser Leu Ile Val Ser Ala Asn
    15              20              25                  30 aca cgt gtt tgg att ggt ggc cat gat ggt gaa act gtaagt cattttgctc   3030
Thr Arg Val Trp Ile Gly Gly His Asp Gly Glu Thr
            35              40 tgaaatgctg atattgtcat ggctagtctg aaattaatgc tttaattata aaactgattt   3090
ttctatagat acaataacta aatgcttttt gttacaatat aaatgattga attatatcat   3150
aaatgaaaag attattagta aactctttga ctctcctcac tcattag    gaa gga caa   3206
                                                       Glu Gly Gln
                                                         1 tgg ctg tgg tct gat gga tct caa ttt cac ttt acc aac tgg tgc cct   3254
Trp Leu Trp Ser Asp Gly Ser Gln Phe His Phe Thr Asn Trp Cys Pro
    5                   10                  15 gga gaa cct agc aat aat ttt ggt aaa gag aac tgc ctg gag ata aac   3302
Gly Glu Pro Ser Asn Asn Phe Gly Lys Glu Asn Cys Leu Glu Ile Asn
    20              25              30                  35 ttt aca cgt aagaaagtc tcatatcatt attgtttta tttacaatct taaaattcta   3360
Phe Thr Arg tagcattttg tattaaattt acttgtttaa tgtcagaaaa tgctacgtgc agtgtattca   3420
ctacattcag atccctttaa cctttcagtg ttgttatttt gcagcctgat ggtacaattg   3480
tttgaattca tacttggttc cccataatga aaaagtgaaa acagaatttt ataaatgtct   3540
gtaaaaaatt ttaaaagaaa aaatgtcaca tttactgtat ttaaaccaag ggtgccaaac   3600
tctgtcttgg agggccggtg gtgacctgtg tagtttagct ctaacactaa tcaaacacac   3660
ctaaagcagt ttattaaagt ctaactaagc atactagaaa cttctagaca ggtgagctga   3720
gacaagttga aactaaactc tgcaggacac cgggcctcta ggaacgagtt tgggcacccc   3780
tgatttagac cctttgcaac aacacttgaa attttgctca gatgcctctt gatcgttgct   3840
gatttataca tttattttta ttcaaactac accggtaatg atcagtactg attttatttt   3900
catcttatcc cacagag    aac cgt tgc tgg aat gat gcg gat tgt tca acc   3950
                      Asn Arg Cys Trp Asn Asp Ala Asp Cys Ser Thr
                        1               5                   10 aca atc agc tac att tgt gcc caa cct att aga tca    tgaa aaatcaatct   4000
Thr Ile Ser Tyr Ile Cys Ala Gln Pro Ile Arg Ser
```

```
               15         20
gtttcaaagt actatgattt tactacatgc ctatacattt ttttctgatc ttattcttaa    4060
aactcagtat cttactgaag ctttctgaaa acttctccaa tcaataaaag catttataaa    4120
gcaaattgtt tgcattgttg agtcaaaaaa attaatcatc aaattaaata caatataaaa    4180
caaaacaaca atacatctaa aataacaaaa agggctttca caattgaaat agttaacctc    4240
aggttattct aaaccccagg tttaaagaat cctgggttat ctgtttcacg tttcacactg    4300
ttcatactta accaggaggt aaagaaataa ccctgggtat tcataatctg atgtttcaca    4360
ctgtgcattt ctaaaccttta agttaatgtt ttcatttgca tatttggggt gtcagcaatt    4420
taaggaagtt tcttcacctc ctcattagca tccagacagc agaagtaggg aactgagcag    4480
cgttcatgac tgaggttctc ttcagaacaa ctgaagtaca ttgagactaa tccatgtaag    4540
agattcctcc acagccagtg gcatgtttac cattttgggg gtcctaagca aagttcaaga    4600
accgggcccc cccatgcccc agcattgccc aaggttttc atttgaattg cacaacaata    4660
acattcagta tacagaatta agttagatat atataaaccg ggtttattta gttgtaccct    4720
gcttaaagta acactaaatt gttacagtat gacaaagatt cttatagatt catatataga    4780
tgtcttagga tgtatttaaa acaatgtaat taatactgca acttcagtgt ctgacatctt    4840
actaaaaaaa ctaaatgagg aaaaagagga agcattagat tatgattcag actggtctaa    4900
caaacaccag caaacaatat tgtaagttgg ttaatgcttg acttaatgga tgggaatcac    4960
ataactctca tgttcatatt gcaaaaacaa acttactgtg agatacaaca agcatataga    5020
ctagacatac actaaagatg agattttaat gacaatgatg agatacagaa tatgatttat    5080
gtattttcga catgtgtggt gtctttatca tgttaatacc tgtacgagca tggaacaaaa    5140
gatgcgtgaa tgttgtgcag ttatgagagc aaagatagag tcgtgtgagc gctcattcca    5200
gcacttgtgt ggctgcattt tgcgcgctg agcagaggtc cgctttcccg tagagcttcg    5260
ttcatgaagt agcctttatg tgcccttgca aggatgtggg caaatattat tctgcgtgca    5320
tactcacaca tctctccctc gcacgtgctt tatccgtacc ttagatttgg ttctgaataa    5380
acctaacata ctttcgcaca ccttgtggcc agtaggggc ccccaagcct gcgggcccta    5440
cgcaattgca tggtttgcgt ggtgggtaaa cacgccactg gttacattgc aagatacttt    5500
gtaaaaaaat gttaatctgt taatagtgcc ctattttaac aatctaagtg catggtctaa    5560
agtgcaaaag ggtttgtcct aatccacttc tgctaattta acgacgggac aaattttggg    5620
gcgtctagcg cactgtctta aagggttgtt cctattctag taatgagtaa tgggtgtgtt    5680
ttgggcatga gttcgattca atgttatttta tataaagctt ttcacaattg tttaattgtt    5740
tcaaagcagc tttacattaa aatatatatt actgtttttt taaactgatg taagattgac    5800
acgaacagtg attgttgatt tgtatgtgca tcaaggcaag gcaagtttat ttgtatagca    5860
catttcatac acagaggtca ttcaaggtgc tttcataga aatgagaaaa caatatatga    5920 gaaaaaagt atgtagaaaa aaatcaaaga tacatttgaa tttaaaatat caattaaaag    5980
aaaataaatg tgatttttaat agaaactgtt taaatgtgtg aaaaaaataa agtataaaac    6040
agtaaaaaaa aattattatt atttagctca gtgggaccat atacaggttg aacaggagtg    6100
cttcggacaa cctgacaatt gtcagaatag atcagagaat tgcctggaaa taaactttttg    6160 aagtaagaat gtctattatt attgtttttta ttataatcttt aacatttttat aggatttagt    6220 acacaataag ccagtttagc tgtcagaaaa tgttacgtgc agtgcattca ctacattcag    6280 atcccttttca ttttattttttg ttcaatgttg tgtagtgatt ttgacacgag caccaattaa    6340
```

```
tttagtgatt tcacatggg caaccattgg ttagtagtat gccatacaca ggacactaga    6400
ggtttcagaa gtacatgctg ggaccaaaga gaccttatta gtactgtcac ggtaggaaat    6460
cctctgtttc ctccgtgtca tgtttgtgtg tgtgtgtgtt tgttactctc tgctctgcca    6520
tgtgctcgtt aggctgatgt cgctcacctg tgtgttgatt gcctcgctcc agctgctcat    6580
cattacatct cctccataaa tactcacatg actctctgtt ccctgccaga tgatcacttt    6640
ctgtttggtc ctcgtgttgt gtggttctac gtctcagtct tggattacga gttgcattgt    6700
ggattgttta ttgtcgtcgt cgtcttcgtg tggatgttcc gtgtacagtc tggattcacc    6760
actgctcacc actccaccaa cgccgcactc aataaccacc taccaccgta gtcctcgtca    6820
ccattgccaa caacaccgga catttcctgc ttgtgtcatt tctctctctg tgttttataaa    6880 taaacattgt gttttcacct gcaattgctt ccgctcagtt cgtgtcatta cagaatcatc    6940
tggccataca tggaagcagc aggagaccaa cccacggcca cgctggagga atttctccag    7000
cgaactctgg ctcgtatgga tcttcaggac cagtcgatca acgaaatgcg ataggccgtc    7060
catgcaatga tgacgaaggt gtccgagctc tctcagcgtt cctctcatcc ttcgcctccc    7120
actgcgccac ccacaccgcc cgcaccatct tctcctccaa ggggtggttt tcctccggag    7180
ccccgattac cgatccctga gaaatactcc ggtgagccaa atta                    7224

<210> SEQ ID NO 3
<211> LENGTH: 21
<212> TYPE: PRT
<213> ORGANISM: Misgurnus mizolepis

<400> SEQUENCE: 3

Met Ala Val Met Arg Ala Leu Val Leu Leu Phe Leu Val Phe Ser Val
 1               5                  10                  15

Glu Ser Ala Pro Gly
            20

<210> SEQ ID NO 4
<211> LENGTH: 28
<212> TYPE: PRT
<213> ORGANISM: Misgurnus mizolepis

<400> SEQUENCE: 4

His Arg Cys Pro His Gly Trp Thr Pro Phe Gly Val Gln Cys Tyr Lys
 1               5                  10                  15

Phe Phe Ser Gln Ser Val Asp Trp Ile Thr Ala Glu
            20                  25

<210> SEQ ID NO 5
<211> LENGTH: 42
<212> TYPE: PRT
<213> ORGANISM: Misgurnus mizolepis

<400> SEQUENCE: 5

Lys Asn Cys Gln Ser Ile Asp Ala Asn Leu Ala Ser Val Arg Ser Thr
 1               5                  10                  15

Met Glu His Asn Phe Leu Leu Ser Leu Ile Val Ser Ala Asn Thr Arg
            20                  25                  30

Val Trp Ile Gly Gly His Asp Gly Glu Thr
        35                  40

<210> SEQ ID NO 6
<211> LENGTH: 38
```

```
<212> TYPE: PRT
<213> ORGANISM: Misgurnus mizolepis

<400> SEQUENCE: 6

Glu Gly Gln Trp Leu Trp Ser Asp Gly Ser Gln Phe His Phe Thr Asn
 1               5                  10                  15

Trp Cys Pro Gly Glu Pro Ser Asn Asn Phe Gly Lys Glu Asn Cys Leu
            20                  25                  30

Glu Ile Asn Phe Thr Arg
        35

<210> SEQ ID NO 7
<211> LENGTH: 23
<212> TYPE: PRT
<213> ORGANISM: Misgurnus mizolepis

<400> SEQUENCE: 7

Asn Arg Cys Trp Asn Asp Ala Asp Cys Ser Thr Thr Ile Ser Tyr Ile
 1               5                  10                  15

Cys Ala Gln Pro Ile Arg Ser
            20

<210> SEQ ID NO 8
<211> LENGTH: 19
<212> TYPE: DNA
<213> ORGANISM: Artificial Sequence
<220> FEATURE:
<223> OTHER INFORMATION: primer for amplifying a lectin gene regulation
      site of a mud loach

<400> SEQUENCE: 8
ggaaaagtga cacatctgc                                               19

<210> SEQ ID NO 9
<211> LENGTH: 19
<212> TYPE: DNA
<213> ORGANISM: Artificial Sequence
<220> FEATURE:
<223> OTHER INFORMATION: primer for amplifying a lectin gene regulation
      site of a mud loach

<400> SEQUENCE: 9
ggaaaagtga cacatctgc                                               19

<210> SEQ ID NO 10
<211> LENGTH: 22
<212> TYPE: DNA
<213> ORGANISM: Artificial Sequence
<220> FEATURE:
<223> OTHER INFORMATION: primer for detecting a BFP gene

<400> SEQUENCE: 10
ggccacaagt tctctgtcag tg                                           22

<210> SEQ ID NO 11
<211> LENGTH: 20
<212> TYPE: DNA
<213> ORGANISM: Artificial Sequence
<220> FEATURE:
<223> OTHER INFORMATION: primer for detecting a BFP gene

<400> SEQUENCE: 11
gggcagattg tgtggacagg                                              20
```

-continued

<210> SEQ ID NO 12
<211> LENGTH: 20
<212> TYPE: DNA
<213> ORGANISM: Artificial Sequence
<220> FEATURE:
<223> OTHER INFORMATION: primer for detecting a CAT gene

<400> SEQUENCE: 12
ctataaccag accgttcagc                                               20

<210> SEQ ID NO 13
<211> LENGTH: 25
<212> TYPE: DNA
<213> ORGANISM: Artificial Sequence
<220> FEATURE:
<223> OTHER INFORMATION: primer for detecting a CAT gene

<400> SEQUENCE: 13
cgccccgccc tgccactcat cgcag                                         25

<210> SEQ ID NO 14
<211> LENGTH: 33
<212> TYPE: DNA
<213> ORGANISM: Artificial Sequence
<220> FEATURE:
<223> OTHER INFORMATION: primer for amplifying a growth hormone gene of
      a carp

<400> SEQUENCE: 14
ccgcggacaa acattcacaa gctcttaact aag                                33

<210> SEQ ID NO 15
<211> LENGTH: 29
<212> TYPE: DNA
<213> ORGANISM: Artificial Sequence
<220> FEATURE:
<223> OTHER INFORMATION: primer for amplifying a growth hormone gene of
      a carp

<400> SEQUENCE: 15
ttctctatta aagttttaaa ttgcatcca                                     29

<210> SEQ ID NO 16
<211> LENGTH: 19
<212> TYPE: DNA
<213> ORGANISM: Artificial Sequence
<220> FEATURE:
<223> OTHER INFORMATION: primer for detecting a lectin gene regulation
      site of a mud loach

<400> SEQUENCE: 16
gttatggagt ccctcccac                                                19

<210> SEQ ID NO 17
<211> LENGTH: 19
<212> TYPE: DNA
<213> ORGANISM: Artificial Sequence
<220> FEATURE:
<223> OTHER INFORMATION: primer for detecting a growth hormone gene of
      a mud loach

<400> SEQUENCE: 17
cagccagctg gtgcaggtg                                                19

<210> SEQ ID NO 18
<211> LENGTH: 23
<212> TYPE: DNA

-continued

```
<213> ORGANISM: Artificial Sequence
<220> FEATURE:
<223> OTHER INFORMATION: primer for detecting a growth hormone gene of
      a carp

<400> SEQUENCE: 18
acaacacctg caccagctgg ctg                                            23
```